(12) United States Patent
Kaneko et al.

(10) Patent No.: US 12,391,739 B2
(45) Date of Patent: Aug. 19, 2025

(54) METHOD FOR PRODUCING GAMMA DELTA T CELLS

(71) Applicants: Kyoto University, Kyoto (JP); Takeda Pharmaceutical Company Limited, Osaka (JP)

(72) Inventors: Shin Kaneko, Kyoto (JP); Shoichi Iriguchi, Kyoto (JP); Tatsuki Ueda, Kyoto (JP); Yoshiaki Kassai, Kanagawa (JP); Akira Hayashi, Kanagawa (JP); Kazuhide Nakayama, Kanagawa (JP)

(73) Assignees: Kyoto University, Kyoto (JP); Takeda Pharmaceutical Company Limited, Osaka (JP)

( * ) Notice: Subject to any disclaimer, the term of this patent is extended or adjusted under 35 U.S.C. 154(b) by 1201 days.

(21) Appl. No.: 17/259,736

(22) PCT Filed: Jul. 12, 2019

(86) PCT No.: PCT/JP2019/027697
§ 371 (c)(1),
(2) Date: Jan. 12, 2021

(87) PCT Pub. No.: WO2020/013315
PCT Pub. Date: Jan. 16, 2020

(65) Prior Publication Data
US 2021/0130777 A1   May 6, 2021

(30) Foreign Application Priority Data

Jul. 13, 2018 (JP) .................... 2018-133727
Jun. 25, 2019 (JP) .................... 2019-117891

(51) Int. Cl.
| | | |
|---|---|---|
| *C07K 14/725* | (2006.01) | |
| *A61K 39/00* | (2006.01) | |
| *A61K 40/11* | (2025.01) | |
| *A61K 40/31* | (2025.01) | |
| *A61K 40/32* | (2025.01) | |
| *A61K 40/35* | (2025.01) | |
| *A61K 40/42* | (2025.01) | |
| *A61K 48/00* | (2006.01) | |
| *A61P 35/00* | (2006.01) | |
| *C07K 14/54* | (2006.01) | |
| *C07K 16/28* | (2006.01) | |
| *C12N 5/0783* | (2010.01) | |
| *C12N 5/10* | (2006.01) | |

(52) U.S. Cl.
CPC .......... *C07K 14/7051* (2013.01); *A61K 40/11* (2025.01); *A61K 40/31* (2025.01); *A61K 40/4211* (2025.01); *A61P 35/00* (2018.01); *C07K 14/5443* (2013.01); *C12N 5/0636* (2013.01); *A61K 2239/48* (2023.05)

(58) Field of Classification Search
CPC ............. C12N 5/0636; C12N 2500/38; C12N 2501/125; C12N 2506/45; C12N 2500/25; C12N 2501/145; C12N 2501/21; C12N 2501/2302; C12N 2501/2315; C12N 2501/2321; C12N 2501/26; C12N 2501/48; C12N 2501/599; C12N 2501/727; C12N 2510/00; C12N 5/10; A61P 35/00; C07K 14/5443; C07K 14/7051; C07K 2317/622; C07K 16/2803; C07K 2319/03; C07K 2319/00; A61K 2239/48; A61K 39/4611; A61K 39/4631; A61K 39/464412; A61K 2039/55527; A61K 2039/572; A61K 48/00

See application file for complete search history.

(56) References Cited

U.S. PATENT DOCUMENTS

| | | | | |
|---|---|---|---|---|
| 9,206,394 | B2* | 12/2015 | Nakauchi | A61K 39/21 |
| 10,660,915 | B2* | 5/2020 | Kaneko | C12N 5/10 |
| 11,401,504 | B2* | 8/2022 | Kawamoto | A61K 2239/48 |
| 11,559,548 | B2* | 1/2023 | Kaneko | C12N 5/0647 |
| 11,578,310 | B2* | 2/2023 | Kaneko | C12N 5/0636 |
| 11,987,811 | B2* | 5/2024 | Kaneko | A61K 39/4611 |
| 2010/0009447 | A1 | 1/2010 | Okamura et al. | |
| 2012/0135525 | A1† | 5/2012 | Rajesh | |
| 2017/0267972 | A1† | 9/2017 | Kawamoto | |
| 2017/0326175 | A1† | 11/2017 | Kaneko | |
| 2017/0333480 | A1* | 11/2017 | Cooper | A61K 39/0011 |
| 2017/0369850 | A1* | 12/2017 | Kaneko | A61K 39/4611 |
| 2019/0330596 | A1 | 10/2019 | Kaneko et al. | |

(Continued)

FOREIGN PATENT DOCUMENTS

| | | |
|---|---|---|
| JP | 2010017134 A | 1/2010 |
| JP | 2017535284 A | 11/2017 |

(Continued)

OTHER PUBLICATIONS

Watanabe et al., Development of IPSC-Based ydeltaT-Cell Immunotherapy for Digestive Cancer. Gastroenterology. Apr. 2017; 152(5 Suppl 1):S641, Abstract Su2054. (Year: 2017).*

(Continued)

*Primary Examiner* — Janet L Epps-Smith
*Assistant Examiner* — Lea S O'Brien
(74) *Attorney, Agent, or Firm* — McCarter & English, LLP; David G. Conlin

(57) ABSTRACT

The present invention provides a method for producing a γδT cell from an induced pluripotent stem cell, wherein the induced pluripotent stem cell is derived from a cell other than an αβT cell.

10 Claims, 7 Drawing Sheets

Specification includes a Sequence Listing.

(56) References Cited

U.S. PATENT DOCUMENTS

| | | | |
|---|---|---|---|
| 2020/0017837 A1 | 1/2020 | Aoi | |
| 2021/0238550 A1* | 8/2021 | Yasui | A61P 35/00 |
| 2022/0411752 A1* | 12/2022 | Kaneko | C12N 15/907 |
| 2023/0000915 A1* | 1/2023 | Kaneko | A61P 35/00 |
| 2023/0183645 A1* | 6/2023 | Kaneko | C12N 15/63 424/93.71 |
| 2023/0357715 A1* | 11/2023 | Kawamoto | C12N 15/63 |
| 2024/0052309 A1* | 2/2024 | Kaneko | A01N 1/0284 |

FOREIGN PATENT DOCUMENTS

| | | | |
|---|---|---|---|
| WO | 2006/006720 A1 | 1/2006 | |
| WO | 2017/041106 A1 | 3/2014 | |
| WO | 2014/165707 A2 | 10/2014 | |
| WO | 2016/073755 A2 | 5/2016 | |
| WO | 2017/075389 A1 | 5/2017 | |
| WO | 2017/221975 A1 | 12/2017 | |
| WO | 2018/135646 A1 | 7/2018 | |
| WO | 2018/143243 A1 | 8/2018 | |
| WO | 2018/147801 A1 | 8/2018 | |

OTHER PUBLICATIONS

Van Acker, Heleen H et al. "Interleukin-15 enhances the proliferation, stimulatory phenotype, and antitumor effector functions of human gamma delta T cells." Journal of hematology & oncology vol. 9,1 101. Sep. 29, 2016, doi: 10.1186/s13045-016-0329-3 (Year: 2016).*

Wu YL, Ding YP, Tanaka Y, Shen LW, Wei CH, Minato N, Zhang W. γδ T Cells and Their Potential for Immunotherapy. Int J Biol Sci 2014; 10(2):119-135. doi: 10.7150/ijbs.7823. https://www.ijbs.com/v10p0119.htm (Year: 2014).*

Kawamoto, H., Masuda, K., Nagano, S et al. Cloning and expansion of antigen-specific T cells using iPS cell technology: development of "off-the-shelf" T cells for the use in allogeneic transfusion settings. Int J Hematol 107, 271-277 (Jan. 31, 2018) (Year: 2018).*

Reimann et al. Human T-Lymphoid Progenitors Generated in a Feeder-Cell-Free Delta-Like-4 Culture System Promote T-Cell Reconstitution in NOD/SCID/γc–/– Mice, Stem Cells, vol. 30, Issue 8, Aug. 2012, pp. 1771-1780 (Year: 2012).*

AOI, Cancer immunotherapy using allogenic iPS cell-derived ydetaIT cells. J Clin Exp Med;Dec. 23, 2017;263(11) 915-919.

Carpenter et al., Differentiating T-Cells from hiPSCs to Create Off-The-Shelf SPEAR T-Cell Therapies. Molecular Therapy. Apr. 2019;27(4S1):460, abstract 990.

Chang et al., Broad T-cell receptor repertoire in T-lymphocytes derived from human induced pluripotent stem cells. PLoS One. May 14, 2014;9(5):e97335, 10 pages.

Smith et al., In Vitro T-Cell Generation From Adult, Embryonic, and Induced Pluripotent Stem Cells: Many Roads to One Destination. Stem Cells. Nov. 2015;33(11):3174-80.

Themeli et al., Generation of tumor-targeted human T lymphocytes from induced pluripotent stem cells for cancer therapy. Nat Biotechnol. Oct. 2013;31(10):928-33.

Watanabe et al., Development of IPSC-Based ydeltaT-Cell Immunotherapy for Digestive Cancer. Gastroenterology. Apr. 2017;152(5 Suppl 1):S641, Abstract Su2054.

Watanabe et al., Development of new gastrointestinal cancer treatment method using iPS cell-derived Vγ9Vdelta2T Cell. Japan Digestive Disease Week, The Japanese Society of Gastroenterology. 2016, Abstract P-413.

Watanabe et al., The Generation of Human ydeltaT Cell-Derived Induced Pluripotent Stem Cells from Whole Peripheral Blood Mononuclear Cell Culture. Stem Cells Transl Med. Jan. 2018;7(1):34-44.

Zeng et al., Derivation of mimetic ydelta T cells endowed with cancer recognition receptors from reprogrammed ydelta T cell. PLoS One. May 9, 2019;14(5):e0216815, 20 pages.

International Search Report and Written Opinion for Application No. PCT/JP2019/027697, dated Oct. 15, 2019, 30 pages.

European Office Action for Application No. 19833471.6, dated Jul. 4, 2022, 9 pages.

Stoklasek et al., Combined IL-15/IL-15Ralpha immunotherapy maximizes IL-15 activity in vivo. J Immunol. Nov. 1, 2006;177(9):6072-80.

Taiwan Search Report for Application No. 108124699, dated Aug. 3, 2023, 4 pages.

Mirzaei et al., Prospects for chimeric antigen receptor (CAR) γδ T cells: A potential game changer for adoptive T cell cancer immunotherapy. Cancer Lett. Oct. 1, 2016;380(2):413-423.

Singapore Office Action for Application No. 11202100260Q, dated Sep. 12, 2022, 9 pages.

Hurton et al., Tethered IL-15 augments antitumor activity and promotes a stem-cell memory subset in tumor-specific cells. Proc Natl Acad Sci U S A. Nov. 29, 2016;113(48):E7788-E7797.

Leca et al., A monoclonal antibody to the Hodgkin's disease-associated antigen CD30 induces activation and long-term growth of human autoreactive gamma delta T cell clone. Cell Immunol. Jun. 1994;156(1):230-9.

Mediavilla-Varela et al., MPL-5821, an ESM-p38 MAPK inhibitor, enhances tumor immune response and M1 microphage polarization in a 3D Ex Vivo system utilizing fresh tumor microspheroids of lung cancer patients. Journal of Immuno Therapy of Cancer. 2017;5(Suppl. 2):87, pp. 166-167, Abstract P333.

Mzcardo et al., Generation of Tumor Antigen-Specific iPSC-Derived Thymic Emigrants Using a 3D Thymic Culture System. Cell Rep. Mar. 20, 2018;22(12):3175-3190.

Yonezawa et al., SDF-1 has costimulatory effects on human T cells: possible involvement of MAPK (ERK2) activation. Microbiol Immunol. 2000;44(2):135-41.

Eurasian Search Report for Application No. 202490423, dated Nov. 20, 2024, 1 page.

Eurasian Search Report for Application No. 202490424, dated Nov. 19, 2024, 1 page.

Eurasian Search Report for Application No. 202490425, dated Nov. 21, 2024, 1 page.

Daisuke Watanabe et al. "The Generation of Human T Cell-Derived Induced Pluripotent Stem Cells from Whole Peripheral Blood Mononuclear Cell Culture" Stem Cells Translational Medicine; vol. 7(1), pp. 34-44; Jan. 2018.†

Mirelle J. A. J. Huijskens et al. "Technical Advance: Ascorbic Acid Induces Development of Double-Positive T Cells from Human Hematopoietic Stem Cells in the Absence of Stromal Cells" Journal of Leukocyte Biology; vol. 96(6), pp. 1165-1175; Dec. 2014.†

Atsutaka Minagawa et al. "Enhancing T Cell Receptor Stability in Rejuvenated iPSC-Derived T Cells Improves Their Use in Cancer Immunotherapy" Cell Stem Cell; vol. 23(6), pp. 850-872; Dec. 6, 2018.†

Nobuyuki Murai et al. "Re-Generation of Cytotoxic T Cells with Distinctive Signatures from Human T-Derived iPSCs" Stem Cell Reports, vol. 18(4), pp. 853-868; Apr. 11, 2023.†

* cited by examiner
† cited by third party

SEQUENCE LISTING

<160> NUMBER OF SEQ ID NOS: 7

<210> SEQ ID NO 1
<211> LENGTH: 965
<212> TYPE: PRT
<213> ORGANISM: Artificial Sequence
<220> FEATURE:
<223> OTHER INFORMATION: CD19-CAR(CD8-CD28-CD30-CD3z)

<400> SEQUENCE: 1

```
Met Asp Trp Thr Trp Arg Ile Leu Phe Leu Val Ala Ala Thr Gly
1               5                   10                  15

Ala His Ser Asp Ile Gln Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Ser Lys Tyr Leu Asn Trp Tyr Gln Gln Lys Pro Asp Gly Thr Val Lys
50                      55                  60

Leu Leu Ile Tyr His Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
                100                 105                 110

Leu Pro Tyr Thr Phe Gly Gly Gly Thr Lys Leu Glu Ile Thr Gly Gly
        115                 120                 125

Gly Gly Ser Gly Gly Gly Ser Gly Gly Gly Ser Glu Val Lys
    130                 135                 140

Leu Gln Glu Ser Gly Pro Gly Leu Val Ala Pro Ser Gln Ser Leu Ser
145                 150                 155                 160

Val Thr Cys Thr Val Ser Gly Val Ser Leu Pro Asp Tyr Gly Val Ser
                165                 170                 175

Trp Ile Arg Gln Pro Pro Arg Lys Gly Leu Glu Trp Leu Gly Val Ile
            180                 185                 190

Trp Gly Ser Glu Thr Thr Tyr Tyr Asn Ser Ala Leu Lys Ser Arg Leu
            195                 200                 205

Thr Ile Ile Lys Asp Asn Ser Lys Ser Gln Val Phe Leu Lys Met Asn
        210                 215                 220

Ser Leu Gln Thr Asp Asp Thr Ala Ile Tyr Tyr Cys Ala Lys His Tyr
225                 230                 235                 240

Tyr Tyr Gly Gly Ser Tyr Ala Met Asp Tyr Trp Gly Gln Gly Thr Ser
                245                 250                 255

Val Thr Val Ser Ser Phe Val Pro Val Phe Leu Pro Ala Lys Pro Thr
                260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Asn His Arg Asn Arg Ser Lys Arg Ser Arg Leu Leu
            340                 345                 350

His Ser Asp Tyr Met Asn Met Thr Pro Arg Arg Pro Gly Pro Thr Arg
        355                 360                 365

Lys His Tyr Gln Pro Tyr Ala Pro Pro Arg Asp Phe Ala Ala Tyr Arg
370                 375                 380

Ser His Thr Asn Asn Lys Ile Glu Lys Ile Tyr Ile Met Lys Ala Asp
385                 390                 395                 400

Thr Val Ile Val Gly Thr Val Lys Ala Glu Leu Pro Glu Gly Arg Gly
                405                 410                 415
```

```
Leu Ala Gly Pro Ala Glu Pro Glu Leu Glu Glu Leu Glu Ala Asp
            420             425                 430

His Thr Pro His Tyr Pro Glu Gln Glu Thr Glu Pro Pro Leu Gly Ser
        435                 440                 445

Cys Ser Asp Val Met Leu Ser Val Glu Glu Gly Lys Glu Asp Pro
450                 455                 460

Leu Pro Thr Ala Ala Ser Gly Lys Arg Val Lys Phe Ser Arg Ser Ala
465             470                 475                 480

Asp Ala Pro Ala Tyr Gln Gln Gly Gln Asn Gln Leu Tyr Asn Glu Leu
                485                 490                 495

Asn Leu Gly Arg Arg Glu Glu Tyr Asp Val Leu Asp Lys Arg Arg Gly
            500                 505                 510

Arg Asp Pro Glu Met Gly Gly Lys Pro Arg Arg Lys Asn Pro Gln Glu
            515                 520                 525

Gly Leu Tyr Asn Glu Leu Gln Lys Asp Lys Met Ala Glu Ala Tyr Ser
            530                 535                 540

Glu Ile Gly Met Lys Gly Glu Arg Arg Arg Gly Lys Gly His Asp Gly
545                 550                 555                 560

Leu Tyr Gln Gly Leu Ser Thr Ala Thr Lys Asp Thr Tyr Asp Ala Leu
                565                 570                 575

His Met Gln Ala Leu Pro Pro Arg Leu Glu Gly Gly Gly Glu Gly Arg
            580                 585                 590

Gly Ser Leu Leu Thr Cys Gly Asp Val Glu Glu Asn Pro Gly Pro Arg
            595                 600                 605

Met Leu Leu Leu Val Thr Ser Leu Leu Leu Cys Glu Leu Pro His Pro
610                 615                 620

Ala Phe Leu Leu Ile Pro Arg Lys Val Cys Asn Gly Ile Gly Ile Gly
625                 630                 635                 640

Glu Phe Lys Asp Ser Leu Ser Ile Asn Ala Thr Asn Ile Lys His Phe
                645                 650                 655

Lys Asn Cys Thr Ser Ile Ser Gly Asp Leu His Ile Leu Pro Val Ala
            660                 665                 670

Phe Arg Gly Asp Ser Phe Thr His Thr Pro Pro Leu Asp Pro Gln Glu
            675                 680                 685

Leu Asp Ile Leu Lys Thr Val Lys Glu Ile Thr Gly Phe Leu Leu Ile
690                 695                 700

Gln Ala Trp Pro Glu Asn Arg Thr Asp Leu His Ala Phe Glu Asn Leu
705                 710                 715                 720

Glu Ile Ile Arg Gly Arg Thr Lys Gln His Gly Gln Phe Ser Leu Ala
                725                 730                 735

Val Val Ser Leu Asn Ile Thr Ser Leu Gly Leu Arg Ser Leu Lys Glu
            740                 745                 750

Ile Ser Asp Gly Asp Val Ile Ile Ser Gly Asn Lys Asn Leu Cys Tyr
            755                 760                 765

Ala Asn Thr Ile Asn Trp Lys Lys Leu Phe Gly Thr Ser Gly Gln Lys
            770                 775                 780

Thr Lys Ile Ile Ser Asn Arg Gly Glu Asn Ser Cys Lys Ala Thr Gly
785                 790                 795                 800

Gln Val Cys His Ala Leu Cys Ser Pro Glu Gly Cys Trp Gly Pro Glu
                805                 810                 815

Pro Arg Asp Cys Val Ser Cys Arg Asn Val Ser Arg Gly Arg Glu Cys
            820                 825                 830

Val Asp Lys Cys Asn Leu Leu Glu Gly Glu Pro Arg Glu Phe Val Glu
```

```
            835                 840                 845
Asn Ser Glu Cys Ile Gln Cys His Pro Glu Cys Leu Pro Gln Ala Met
    850                 855                 860

Asn Ile Thr Cys Thr Gly Arg Gly Pro Asp Asn Cys Ile Gln Cys Ala
865                 870                 875                 880

His Tyr Ile Asp Gly Pro His Cys Val Lys Thr Cys Pro Ala Gly Val
                    885                 890                 895

Met Gly Glu Asn Asn Thr Leu Val Trp Lys Tyr Ala Asp Ala Gly His
                900                 905                 910

Val Cys His Leu Cys His Pro Asn Cys Thr Tyr Gly Cys Thr Gly Pro
        915                 920                 925

Gly Leu Glu Gly Cys Pro Thr Asn Gly Pro Lys Ile Pro Ser Ile Ala
    930                 935                 940

Thr Gly Met Val Gly Ala Leu Leu Leu Leu Val Val Ala Leu Gly
945                 950                 955                 960

Ile Gly Leu Phe Met
                965

<210> SEQ ID NO 2
<211> LENGTH: 544
<212> TYPE: PRT
<213> ORGANISM: Artificial Sequence
<220> FEATURE:
<223> OTHER INFORMATION: CD19-CAR(CD8-CD28-4-1BB-CD3z)
<220> FEATURE:
<221> NAME/KEY: lead sequence of immunoglobulin heavy chain
<222> LOCATION: (1)..(22)
<220> FEATURE:
<221> NAME/KEY: variable reagion of anti-CD19 antibody light chain
<222> LOCATION: (23)..(126)
<220> FEATURE:
<221> NAME/KEY: Peptide Linker
<222> LOCATION: (127)..(141)
<220> FEATURE:
<221> NAME/KEY: variable reagion of anti-CD19 antibody heavy chain
<222> LOCATION: (142)..(261)
<220> FEATURE:
<221> NAME/KEY: CD8-derived sequence
<222> LOCATION: (262)..(344)
<220> FEATURE:
<221> NAME/KEY: intracellular domain region of CD28
<222> LOCATION: (345)..(385)
<220> FEATURE:
<221> NAME/KEY: intracellular domain region of 4-1BB
<222> LOCATION: (386)..(432)
<220> FEATURE:
<221> NAME/KEY: intracellular domain region of CD3 zeta
<222> LOCATION: (433)..(544)

<400> SEQUENCE: 2

Met Asp Trp Thr Trp Arg Ile Leu Phe Leu Val Ala Ala Ala Thr Gly
1               5                   10                  15

Ala His Ser Asp Ile Gln Met Thr Gln Thr Thr Ser Ser Leu Ser Ala
                20                  25                  30

Ser Leu Gly Asp Arg Val Thr Ile Ser Cys Arg Ala Ser Gln Asp Ile
            35                  40                  45

Ser Lys Tyr Leu Asn Trp Tyr Gln Gln Lys Pro Asp Gly Thr Val Lys
        50                  55                  60

Leu Leu Ile Tyr His Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
```

```
                100             105             110
Leu Pro Tyr Thr Phe Gly Gly Thr Lys Leu Glu Ile Thr Gly Gly
            115             120             125

Gly Gly Ser Gly Gly Gly Ser Gly Gly Gly Ser Glu Val Lys
            130             135         140

Leu Gln Glu Ser Gly Pro Gly Leu Val Ala Pro Ser Gln Ser Leu Ser
145             150             155             160

Val Thr Cys Thr Val Ser Gly Val Ser Leu Pro Asp Tyr Gly Val Ser
                165             170             175

Trp Ile Arg Gln Pro Pro Arg Lys Gly Leu Glu Trp Leu Gly Val Ile
            180             185             190

Trp Gly Ser Glu Thr Thr Tyr Tyr Asn Ser Ala Leu Lys Ser Arg Leu
            195             200             205

Thr Ile Ile Lys Asp Asn Ser Lys Ser Gln Val Phe Leu Lys Met Asn
            210             215             220

Ser Leu Gln Thr Asp Asp Thr Ala Ile Tyr Tyr Cys Ala Lys His Tyr
225             230             235             240

Tyr Tyr Gly Gly Ser Tyr Ala Met Asp Tyr Trp Gly Gln Gly Thr Ser
                245             250             255

Val Thr Val Ser Ser Phe Val Pro Val Phe Leu Pro Ala Lys Pro Thr
            260             265             270

Thr Thr Pro Ala Pro Arg Pro Pro Thr Pro Ala Pro Thr Ile Ala Ser
            275             280             285

Gln Pro Leu Ser Leu Arg Pro Glu Ala Cys Arg Pro Ala Ala Gly Gly
            290             295             300

Ala Val His Thr Arg Gly Leu Asp Phe Ala Cys Asp Ile Tyr Ile Trp
305             310             315             320

Ala Pro Leu Ala Gly Thr Cys Gly Val Leu Leu Leu Ser Leu Val Ile
                325             330             335

Thr Leu Tyr Cys Asn His Arg Asn Arg Ser Lys Arg Ser Arg Leu Leu
            340             345             350

His Ser Asp Tyr Met Asn Met Thr Pro Arg Arg Pro Gly Pro Thr Arg
            355             360             365

Lys His Tyr Gln Pro Tyr Ala Pro Pro Arg Asp Phe Ala Ala Tyr Arg
            370             375             380

Ser Arg Phe Ser Val Val Lys Arg Gly Arg Lys Lys Leu Leu Tyr Ile
385             390             395             400

Phe Lys Gln Pro Phe Met Arg Pro Val Gln Thr Thr Gln Glu Glu Asp
                405             410             415

Gly Cys Ser Cys Arg Phe Pro Glu Glu Glu Glu Gly Gly Cys Glu Leu
            420             425             430

Arg Val Lys Phe Ser Arg Ser Ala Asp Ala Pro Ala Tyr Gln Gln Gly
            435             440             445

Gln Asn Gln Leu Tyr Asn Glu Leu Asn Leu Gly Arg Arg Glu Glu Tyr
            450             455             460

Asp Val Leu Asp Lys Arg Arg Gly Arg Asp Pro Glu Met Gly Gly Lys
465             470             475             480

Pro Arg Arg Lys Asn Pro Gln Glu Gly Leu Tyr Asn Glu Leu Gln Lys
                485             490             495

Asp Lys Met Ala Glu Ala Tyr Ser Glu Ile Gly Met Lys Gly Glu Arg
            500             505             510

Arg Arg Gly Lys Gly His Asp Gly Leu Tyr Gln Gly Leu Ser Thr Ala
            515             520             525
```

```
                    Thr Lys Asp Thr Tyr Asp Ala Leu His Met Gln Ala Leu Pro Pro Arg
                        530                 535                 540

<210> SEQ ID NO 3
<211> LENGTH: 87
<212> TYPE: PRT
<213> ORGANISM: Homo sapiens

<400> SEQUENCE: 3

His Thr Asn Asn Lys Ile Glu Lys Ile Tyr Ile Met Lys Ala Asp Thr
1               5                   10                  15

Val Ile Val Gly Thr Val Lys Ala Glu Leu Pro Glu Gly Arg Gly Leu
            20                  25                  30

Ala Gly Pro Ala Glu Pro Glu Leu Glu Glu Leu Glu Ala Asp His
        35                  40                  45

Thr Pro His Tyr Pro Glu Gln Glu Thr Glu Pro Leu Gly Ser Cys
    50                  55                  60

Ser Asp Val Met Leu Ser Val Glu Glu Gly Lys Glu Asp Pro Leu
65                  70                  75                  80

Pro Thr Ala Ala Ser Gly Lys
                85

<210> SEQ ID NO 4
<211> LENGTH: 15
<212> TYPE: PRT
<213> ORGANISM: Artificial Sequence
<220> FEATURE:
<223> OTHER INFORMATION: Peptide Linker

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 24
<212> TYPE: PRT
<213> ORGANISM: Artificial Sequence
<220> FEATURE:
<223> OTHER INFORMATION: Peptide Linker

<400> SEQUENCE: 5

Ser Gly Gly Gly Ser Gly Gly Gly Ser Gly Gly Gly Ser Gly
1               5                   10                  15

Gly Gly Gly Ser Gly Gly Gly Ser
            20

<210> SEQ ID NO 6
<211> LENGTH: 400
<212> TYPE: PRT
<213> ORGANISM: Homo sapiens
<220> FEATURE:
<221> NAME/KEY: human IL-2 lead sequence
<222> LOCATION: (1)..(23)
<220> FEATURE:
<221> NAME/KEY: human IL-15
<222> LOCATION: (24)..(137)
<220> FEATURE:
<221> NAME/KEY: Peptide Linker
<222> LOCATION: (138)..(161)
<220> FEATURE:
<221> NAME/KEY: human IL-15Ra
<222> LOCATION: (162)..(400)

<400> SEQUENCE: 6
```

```
Met Tyr Arg Met Gln Leu Leu Ser Cys Ile Ala Leu Ser Leu Ala Leu
1               5                   10                  15

Val Thr Asn Ser Ala Thr Ser Asn Trp Val Asn Val Ile Ser Asp Leu
            20                  25                  30

Lys Lys Ile Glu Asp Leu Ile Gln Ser Met His Ile Asp Ala Thr Leu
        35                  40                  45

Tyr Thr Glu Ser Asp Val His Pro Ser Cys Lys Val Thr Ala Met Lys
    50                  55                  60

Cys Phe Leu Leu Glu Leu Gln Val Ile Ser Leu Glu Ser Gly Asp Ala
65                  70                  75                  80

Ser Ile His Asp Thr Val Glu Asn Leu Ile Ile Leu Ala Asn Asn Ser
                85                  90                  95

Leu Ser Ser Asn Gly Asn Val Thr Glu Ser Gly Cys Lys Glu Cys Glu
            100                 105                 110

Glu Leu Glu Glu Lys Asn Ile Lys Glu Phe Leu Gln Ser Phe Val His
        115                 120                 125

Ile Val Gln Met Phe Ile Asn Thr Ser Ser Gly Gly Gly Ser Gly Gly
    130                 135                 140

Gly Gly Ser Gly Gly Gly Gly Ser Gly Gly Gly Gly Ser Gly Gly Gly
145                 150                 155                 160

Ser Leu Gln Ile Thr Cys Pro Pro Pro Met Ser Val Glu His Ala Asp
                165                 170                 175

Ile Trp Val Lys Ser Tyr Ser Leu Tyr Ser Arg Glu Arg Tyr Ile Cys
                180                 185                 190

Asn Ser Gly Phe Lys Arg Lys Ala Gly Thr Ser Ser Leu Thr Glu Cys
            195                 200                 205

Val Leu Asn Lys Ala Thr Asn Val Ala His Trp Thr Thr Pro Ser Leu
210                 215                 220

Lys Cys Ile Arg Asp Pro Ala Leu Val His Gln Arg Pro Ala Pro Pro
225                 230                 235                 240

Ser Thr Val Thr Thr Ala Gly Val Thr Pro Gln Pro Glu Ser Leu Ser
                245                 250                 255

Pro Ser Gly Lys Glu Pro Ala Ala Ser Ser Pro Ser Ser Asn Asn Thr
            260                 265                 270

Ala Ala Thr Thr Ala Ala Ile Val Pro Gly Ser Gln Leu Met Pro Ser
            275                 280                 285

Lys Ser Pro Ser Thr Gly Thr Thr Glu Ile Ser Ser His Glu Ser Ser
        290                 295                 300

His Gly Thr Pro Ser Gln Thr Thr Ala Lys Asn Trp Glu Leu Thr Ala
305                 310                 315                 320

Ser Ala Ser His Gln Pro Pro Gly Val Tyr Pro Gln Gly His Ser Asp
                325                 330                 335

Thr Thr Val Ala Ile Ser Thr Ser Thr Val Leu Leu Cys Gly Leu Ser
                340                 345                 350

Ala Val Ser Leu Leu Ala Cys Tyr Leu Lys Ser Arg Gln Thr Pro Pro
            355                 360                 365

Leu Ala Ser Val Glu Met Glu Ala Met Glu Ala Leu Pro Val Thr Trp
        370                 375                 380

Gly Thr Ser Ser Arg Asp Glu Asp Leu Glu Asn Cys Ser His His Leu
385                 390                 395                 400

<210> SEQ ID NO 7
<211> LENGTH: 629
<212> TYPE: PRT
```

```
<213> ORGANISM: Artificial Sequence
<220> FEATURE:
<223> OTHER INFORMATION: Vgamma9 Vdelta2 TCR
<220> FEATURE:
<221> NAME/KEY: T cell receptor gamma
<222> LOCATION: (1)..(315)
<220> FEATURE:
<221> NAME/KEY: P2A
<222> LOCATION: (316)..(337)
<220> FEATURE:
<221> NAME/KEY: T cell receptor delta
<222> LOCATION: (338)..(629)

<400> SEQUENCE: 7
```

Met Val Ser Leu Leu His Ala Ser Thr Leu Ala Val Leu Gly Ala Leu
1               5                   10                  15

Cys Val Tyr Gly Ala Gly His Leu Glu Gln Pro Gln Ile Ser Ser Thr
            20                  25                  30

Lys Thr Leu Ser Lys Thr Ala Arg Leu Glu Cys Val Val Ser Gly Ile
        35                  40                  45

Thr Ile Ser Ala Thr Ser Val Tyr Trp Tyr Arg Glu Arg Pro Gly Glu
    50                  55                  60

Val Ile Gln Phe Leu Val Ser Ile Ser Tyr Asp Gly Thr Val Arg Lys
65                  70                  75                  80

Glu Ser Gly Ile Pro Ser Gly Lys Phe Glu Val Asp Arg Ile Pro Glu
                85                  90                  95

Thr Ser Thr Ser Thr Leu Thr Ile His Asn Val Glu Lys Gln Asp Ile
            100                 105                 110

Ala Thr Tyr Tyr Cys Ala Leu Trp Glu Ala Gln Gln Glu Leu Gly Lys
        115                 120                 125

Lys Ile Lys Val Phe Gly Pro Gly Thr Lys Leu Ile Ile Thr Asp Lys
    130                 135                 140

Gln Leu Asp Ala Asp Val Ser Pro Lys Pro Thr Ile Phe Leu Pro Ser
145                 150                 155                 160

Ile Ala Glu Thr Lys Leu Gln Lys Ala Gly Thr Tyr Leu Cys Leu Leu
                165                 170                 175

Glu Lys Phe Phe Pro Asp Val Ile Lys Ile His Trp Glu Glu Lys Lys
            180                 185                 190

Ser Asn Thr Ile Leu Gly Ser Gln Glu Gly Asn Thr Met Lys Thr Asn
        195                 200                 205

Asp Thr Tyr Met Lys Phe Ser Trp Leu Thr Val Pro Glu Lys Ser Leu
    210                 215                 220

Asp Lys Glu His Arg Cys Ile Val Arg His Glu Asn Asn Lys Asn Gly
225                 230                 235                 240

Val Asp Gln Glu Ile Ile Phe Pro Pro Ile Lys Thr Asp Val Ile Thr
                245                 250                 255

Met Asp Pro Lys Asp Asn Cys Ser Lys Asp Ala Asn Asp Thr Leu Leu
            260                 265                 270

Leu Gln Leu Thr Asn Thr Ser Ala Tyr Tyr Met Tyr Leu Leu Leu Leu
        275                 280                 285

Leu Lys Ser Val Val Tyr Phe Ala Ile Ile Thr Cys Cys Leu Leu Arg
    290                 295                 300

Arg Thr Ala Phe Cys Cys Asn Gly Glu Lys Ser Gly Ser Gly Ala Thr
305                 310                 315                 320

Asn Phe Ser Leu Leu Lys Gln Ala Gly Asp Val Glu Glu Asn Pro Gly
                325                 330                 335

Pro Met Glu Arg Ile Ser Ser Leu Ile His Leu Ser Leu Phe Trp Ala

-continued

```
                340                 345                 350
Gly Val Met Ser Ala Ile Glu Leu Val Pro Glu His Gln Thr Val Pro
            355                 360                 365
Val Ser Ile Gly Val Pro Ala Thr Leu Arg Cys Ser Met Lys Gly Glu
        370                 375                 380
Ala Ile Gly Asn Tyr Tyr Ile Asn Trp Tyr Arg Lys Thr Gln Gly Asn
385                 390                 395                 400
Thr Met Thr Phe Ile Tyr Arg Glu Lys Asp Ile Tyr Gly Pro Gly Phe
                405                 410                 415
Lys Asp Asn Phe Gln Gly Asp Ile Asp Ile Ala Lys Asn Leu Ala Val
            420                 425                 430
Leu Lys Ile Leu Ala Pro Ser Glu Arg Asp Glu Gly Ser Tyr Tyr Cys
        435                 440                 445
Ala Cys Asp Thr Leu Gly Met Gly Gly Glu Tyr Thr Asp Lys Leu Ile
        450                 455                 460
Phe Gly Lys Gly Thr Arg Val Thr Val Glu Pro Arg Ser Gln Pro His
465                 470                 475                 480
Thr Lys Pro Ser Val Phe Val Met Lys Asn Gly Thr Asn Val Ala Cys
                485                 490                 495
Leu Val Lys Glu Phe Tyr Pro Lys Asp Ile Arg Ile Asn Leu Val Ser
            500                 505                 510
Ser Lys Lys Ile Thr Glu Phe Asp Pro Ala Ile Val Ile Ser Pro Ser
        515                 520                 525
Gly Lys Tyr Asn Ala Val Lys Leu Gly Lys Tyr Glu Asp Ser Asn Ser
        530                 535                 540
Val Thr Cys Ser Val Gln His Asp Asn Lys Thr Val His Ser Thr Asp
545                 550                 555                 560
Phe Glu Val Lys Thr Asp Ser Thr Asp His Val Lys Pro Lys Glu Thr
                565                 570                 575
Glu Asn Thr Lys Gln Pro Ser Lys Ser Cys His Lys Pro Lys Ala Ile
            580                 585                 590
Val His Thr Glu Lys Val Asn Met Met Ser Leu Thr Val Leu Gly Leu
        595                 600                 605
Arg Met Leu Phe Ala Lys Thr Val Ala Val Asn Phe Leu Leu Thr Ala
        610                 615                 620
Lys Leu Phe Phe Leu
625
```

METHOD FOR PRODUCING GAMMA DELTA T CELLS

RELATED APPLICATIONS

This application is a national stage application filed under 35 U.S.C. § 371 of International Patent Application No. PCT/JP2019/027697, filed Jul. 12, 2019 designating the United States, which claims the benefit of and priority to Japanese Patent Application No. 2018-133727, filed Jul. 13, 2018 and Japanese Patent Application No. 2019-117891, filed Jun. 25, 2019, the entire contents of which are hereby expressly incorporated by reference herein.

INCORPORATION BY REFERENCE OF SEQUENCE LISTING

The contents of the text file named "048504-605N01US_Sequence_Listing_ST25", which was created on Jan. 11, 2021 and is in 24.1 KB in size, are hereby incorporated by reference in their entireties and for all purposes.

TECHNICAL FIELD

The present invention relates to a method for producing γδT cells from induced pluripotent stem cells, γδT cells differentiated from induced pluripotent stem cells, a cell population containing the cells, and the like.

BACKGROUND OF THE INVENTION

In recent years, immune cell therapy has been attracting attention as a treatment method for cancer. Immune cell therapy is a therapeutic method including proliferating and activating immune cells outside the patient's body and administering the immune cells to the patient to allow the immune cells to attack the cancer cells. Immune cell therapy is advantageous in that it causes almost no side effects compared to the conventional three major therapies of surgical treatment, radiation therapy, and chemotherapy. There are various kinds of treatment methods for immune cell therapy. Among them, a treatment using γδT cell, which is responsible for natural immunity and has cytotoxic activity against cancer cells, is attracting attention.

In γδT cell therapy, the development of a production method for efficiently producing and stably supplying the cell is desired to achieve the cell therapy. While a method of selecting only γδT cells in the patient's blood (a method of culturing blood cells in a medium containing zoledronic acid and IL-2 (patent document 1)) is known, a method for producing γδT cells from stem cells has not been reported as far as the present inventors are aware.

DOCUMENT LIST

Patent Document

[patent document 1] WO 2006/006720

SUMMARY OF INVENTION

Technical Problem

A problem of the present invention is to provide a method for producing γδT cells from stem cells. It is also a problem of the present invention to provide γδT cells differentiated from stem cells and a cell population containing the cells.

Solution to Problem

The present inventors have conducted intensive studies in an attempt to solve the aforementioned problems and found that γδT cells can be efficiency obtained by inducing pluripotent stem cells from cells other than αβT cells and further inducing the cells into T cells. In addition, γδT cells expressing chimeric antigen receptor (CAR) were prepared by introducing the CAR gene into the thus-obtained γδT cells. It was revealed that the γδT cells show high cytotoxicity even to cancer cells that are difficult to recognize and damage with the γδT cells before introduction. The present inventors conducted further studies based on these findings and completed the present invention.

Therefore, the present invention provides the following.

[1] A method for producing a γδT cell from an induced pluripotent stem cell, wherein the induced pluripotent stem cell is derived from a cell other than an αβT cell.

[2] The method of [1], comprising the following steps:
(1) a step for establishing an induced pluripotent stem cell from a cell other than an αβT cell, and
(2) a step for differentiating the induced pluripotent stem cell established in step (1) into a T cell.

[3] The method of [1] or [2], wherein the cell other than an αβT cell is a mononuclear cell other than an αβT cell.

[4] The method of any one of [1] to [3], wherein the cell other than an αβT cell is a monocyte.

[5] The method of any one of [2] to [4], comprising a step for introducing
(i) a nucleic acid encoding αTCR and a nucleic acid encoding βTCR,
(ii) a nucleic acid encoding γTCR and a nucleic acid encoding δTCR, and/or
(iii) a nucleic acid encoding CAR,
each of which recognizes and binds to a tumor-specific antigen or a tumor-associated antigen, into the cell obtained in any of the steps (1) and (2).

[6] The method of [5], wherein the γTCR is Vγ9TCR and the δTCR is Vδ2TCR.

[7] The method of any one of [1] to [6], comprising a step of 25 introducing a nucleic acid encoding a fusion protein comprising IL-15 and IL-15Rα into the cell obtained in any of the steps (1) and (2).

[8] A γδT cell derived from an induced pluripotent stem cell, wherein the induced pluripotent stem cell is derived from a cell other than an αβT cell.

[9] A γδT cell produced by the method of any one of [1] to [7].

[10] The cell of [8] or [9], wherein the cell other than an αβT cell is a mononuclear cell other than an αβT cell.

[11] The cell of any one of [8] to [10], wherein the cell other than an αβT cell is a monocyte.

[12] The cell of any one of [8] to [11], wherein the γδT cell expresses Vγ9TCR and Vδ2TCR.

[13] The cell of any one of [8] to [12], wherein the γδT cell expresses CAR.

[14] The cell of any one of [8] to [13], wherein the γδT cell expresses a fusion protein comprising IL-15 and IL-15Rα.

[15] A cell population in which not less than 90% of all cells are γδT cells, wherein the γδT cell is a cell differentiated from an induced pluripotent stem cell derived from a cell other than an αβT cell.

[16] A medicament comprising the cell of any one of [8] to [14] or the cell population of [15].
[17] The medicament of [16] for use in the prevention or the treatment of tumor.
[18] A killing agent for a cell, comprising the cell of any one of [8] to [14] or the cell population of [15].
[19] The cell of any one of [8] to [14] or the cell population of [15], for use in the prevention or the treatment of tumor.
[20] Use of the cell of any one of [8] to [14] or the cell population of [15] in the manufacture of a preventive agent or therapeutic agent for tumor.
[21] A method for preventing or treating tumor, comprising administering the cell of any one of [8] to [14] or the cell population of [15].

Advantageous Effects of Invention

According to the present invention, a method for producing γδT cells from induced pluripotent stem cells, γδT cells differentiated from induced pluripotent stem cells, a cell population containing the cells, and the like can be provided. Furthermore, among the γδT cells produced by the above-mentioned method, the cells expressing chimeric antigen receptor (CAR) can show in vitro and in vivo high cytotoxic activity specific to the antigen recognized by CAR.

DETAILED DESCRIPTION OF THE INVENTION

Figure 1:
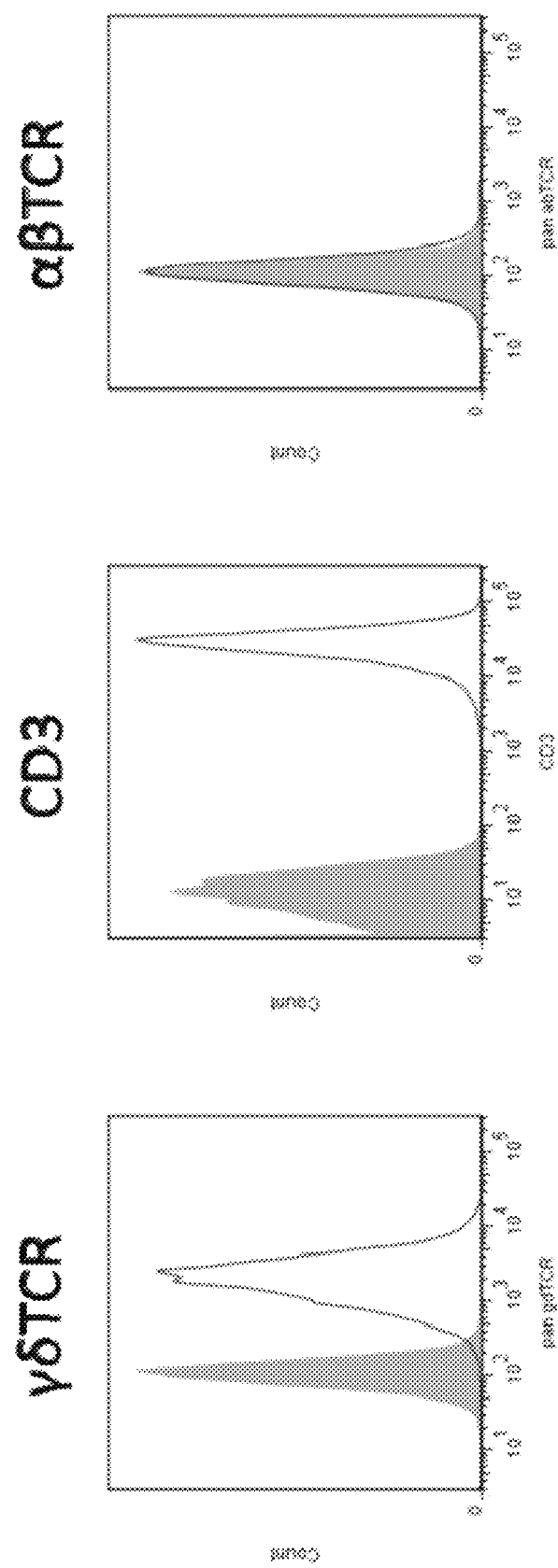
FIG. 1 shows the results obtained by staining the acquired cells by using an antibody set (Vδ1 Myltenyi FITC, Vδ2 Myltenyi APC, γδTCR BD BV510, CD3 BioLegend APC/Cy7 and αβTCR eBioscience FITC). The filled peaks show the results of the non-staining group, and the blank peaks show the staining results using each antigen-specific antibody.

In the present specification, the "gene expression" encompasses both the synthesis of mRNA from a specific nucleotide sequence of the gene (also referred to as transcription or mRNA expression) and the synthesis of protein based on the information of the mRNA (also referred to as translation or protein expression). Unless otherwise specified, the "gene expression" or simple "expression" means expression of protein.

In the present specification, "positive" means that a protein or mRNA is expressed in an amount detectable by a method known in the art. Protein can be detected by an immunological assay using an antibody, such as ELISA, immunostaining, and flow cytometry. In the case of a protein that is intracellularly expressed and does not appear on the cell surface (e.g., transcription factor or subunit thereof, and the like), a reporter protein is expressed together with the protein, and the target protein can be detected by detecting the reporter protein. mRNA can be detected by, for example, nucleic acid amplification method and/or nucleic acid detection method such as RT-PCR, microarray, biochip, RNAseq and the like.

In the present specification, "negative" means that the expression level of the protein or mRNA is less than the lower limit of detection by all or any of the above-mentioned known methods. The lower limit of detection of protein or mRNA expression may vary depending on each method.

In the present specification, positive is also indicated as "expressing protein or mRNA", and negative is also indicated as "not expressing protein or mRNA". Therefore, adjustment of the "presence or absence of expression" means placing the cell in a state where the expression level of the detection target protein or mRNA is not less than the detection lower limit (positive) or less than the detection lower limit (negative).

In the present specification, the "culture" refers to maintaining, proliferating (growing) and/or differentiating cells in an in vitro environment. "Culture" means maintaining, proliferating (growing) and/or differentiating cells extra-tissue or ex-vivo, for example, in a cell culture plate, dish or flask.

In the present specification, "concentrating" refers to increasing the proportion of a particular constituent component in a composition such as a cell composition and the like, and "concentrated" when used to describe a cell composition such as a cell population means that the amount of a particular constituent component in the cell population has increased from that of the component in the cell population before being concentrated. For example, a composition such as cell population and the like can be concentrated for the target cell type. Thus, the proportion of the target cell type increase as compared to the proportion of the target cell present in the cell population before being concentrated. A cell population may also be concentrated for the target cell type by a cell selecting method or sorting method known in the art. The cell population may also be concentrated by a particular culture method, sorting, or a selecting process, described in the present specification. In a particular embodiment of the present invention, the cell population is concentrated by at least 10%, 20%, 30%, 40%, 50%, 60%, 70%, 80%, 85%, 90%, 95%, 97%, 98% or 99% of the target cell population by a method of concentrating the target cell population.

In the present specification, the "expansion culture" means culturing for the purpose of proliferating a desired cell population and increasing the cell number. The increase in cell number may be achieved by increasing the number of cells by proliferation to exceed the decrease in number by death, and it does not require proliferation of all cells in the cell population. The increase in the cell number may be 1.1 times, 1.2 times, 1.5 times, 2 times, 3 times, 4 times, 5 times, 6 times, 7 times, 8 times, 9 times, 10 times, 15 times, 20 times, 30 times, 40 times, 50 times, 100 times, 300 times, 500 times, 1,000 times, 3,000 times, 5,000 times, 10,000 times, 100,000 times, or not less than 1,000,000 times, compared to that before the start of expansion culture.

In the present specification, "stimulation" means that a certain substance binds to various receptors and the like to activate a signal pathway at the downstream thereof.

In the present specification, the "cell population" means two or more cells of the same type or different types. The "cell population" also means a mass of cells of the same type or different types.

1. Method for Producing γδT Cells from Induced Pluripotent Stem Cells

The present invention provides a method for producing γδT cells from induced pluripotent stem cells, and a cell population containing the γδT cells (hereinafter sometimes to be abbreviated as "the production method of the present invention"). The production method of the present invention includes a step for differentiating induced pluripotent stem cells into T cells. Induced pluripotent stem cells used for the production method of the present invention may be cells already established and stocked, and the induced pluripotent stem cells may be established from a cell other than an αβT cell. In one embodiment of the present invention, therefore, the production method of the present invention includes (1) a step for establishing the induced pluripotent stem cell from a cell other than an αβT cell and (2) a step for differentiating the induced pluripotent stem cell established in step (1) into a T cell.

In the present invention, the "T cell receptor (TCR)" is constituted of a dimer of TCR chains (α chain, β chain, γ chain, δ chain). The "γδT cell" means a cell that expresses CD3, and expresses TCR constituted of TCRγ chain (γTCR) and TCRδ chain (δTCR) (hereinafter sometimes to be referred to as "γδTCR"). The "αβT cell" means a cell that expresses CD3, and expresses TCR constituted of TCRα chain (αTCR) and TCRδ chain (βTCR) (hereinafter sometimes to be referred to as "αβTCR"). Almost all αβT cells recognize antigen peptide-MHC (major histocompatibility complex, in the case of human, HLA: human leukocyte antigen) complex by αβTCR (this is to be referred to as MHC restriction). In contrast, γδT cell recognizes various molecules expressed by cells, by γδTCR regardless of MHC molecule. Each TCR chain is constituted of a variable region and a constant region, and the variable region contains three complementarity determining regions (CDR1, CDR2, CDR3). TCR gene is constituted of many V (variable), D (diversity), J (joining) and C (constant) gene segments on the genome. Gene reconstitution is carried out during the process of differentiation and maturation of T cells, one each of D and J are randomly selected and bound in β chain gene, then gene reconstitution occurs between V-DJ. During the process, insertion and deletion of base randomly occurs between V-D and D-J, and gene variety increases. In TCR mRNA precursor, RNA splicing occurs in the VDJ region and the C region (a common region), and the gene is expressed as a functional TCR gene.

Examples of the γTCR include Vγ1TCR, Vγ2TCR, Vγ3TCR, Vγ4TCR, Vγ5TCR, Vγ6TCR, Vγ7TCR, Vγ8TCR, and Vγ9TCR, and examples of the δTCR include Vδ1TCR, VΩTCR, Vδ3TCR, Vδ4TCR, Vδ5TCR, Vδ6TCR, Vδ7TCR, Vδ8TCR, and Vδ9TCR. While the combination of specific γTCR and δTCR is not limited, for example, Vγ3Vδ1TCR, Vγ4Vδ1TCR, Vγ9Vδ1TCR, and Vγ9V2TCR can be mentioned.

(1) Step for Establishing Induced Pluripotent Stem Cell

In the present invention, the "induced pluripotent stem cell" (hereinafter sometimes to be referred to as "iPS cell") means a stem cell that is established by introducing a reprogramming factor into a somatic cell, has pluripotency permitting differentiation into many cells present in living organisms, and also has proliferation capacity. It encompasses any cell induced into a hematopoietic progenitor cell to be used in the present invention. The induced pluripotent stem cell is preferably derived from a mammal (e.g., mouse, rat, hamster, guinea pig, dog, monkey, orangutan, chimpanzee, human), more preferably human.

A method for establishing an induced pluripotent stem cell is known in the pertinent field, and the cell can be established by introducing a reprogramming factor into any somatic cell. As used herein, the reprogramming factor includes, for example, genes and gene products such as Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, Glis1 and the like. These reprogramming factors may be used alone or in combination. The combination reprogramming factor is exemplified by the combinations described in WO 2007/069666, WO 2008/118820, WO 2009/007852, WO 2009/032194, WO 2009/058413, WO 2009/057831, WO 2009/075119, WO 2009/079007, WO 2009/091659, WO 2009/101084, WO 2009/101407, WO 2009/102983, WO 2009/114949, WO 2009/117439, WO 2009/126250, WO 2009/126251, WO 2009/126655, WO 2009/157593, WO 2010/009015, WO 2010/033906, WO 2010/033920, WO 2010/042800, WO 2010/050626, WO 2010/056831, WO 2010/068955, WO 2010/098419, WO 2010/102267, WO 2010/111409, WO 2010/111422, WO 2010/115050, WO 2010/124290, WO 2010/147395, WO 2010/147612, Huangfu D, et al. (2008), Nat. Biotechnol., 26: 795-797, Shi Y, et al. (2008), Cell Stem Cell, 2: 525-528, Eminli S, et al. (2008), Stem Cells. 26:2467-2474, Huangfu D, et al. (2008), Nat. Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat. Cell Biol. 11:197-203, R. L. Judson et al., (2009), Nat. Biotechnol., 27:459-461, Lyssiotis C A, et al. (2009), Proc Natl Acad Sci USA. 106:8912-8917, Kim J B, et al. (2009), Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, Mali P, et al. (2010), Stem Cells. 28:713-720, and Maekawa M, et al. (2011), Nature. 474:225-9.

Examples of the somatic cells include, but are not limited to, any of fetal somatic cells, neonatal somatic cells, and mature somatic cells, as well as any of primary cultured cells, subcultured cells, and established cell lines. Furthermore, the cells described above may be healthy cells or diseased cells. Specific examples of the somatic cells include (1) tissue stem cells (somatic stem cells) such as neural stem cells, hematopoietic progenitor cells, mesenchymal stem cells, and dental pulp stem cells; (2) tissue progenitor cells; and (3) differentiated cells such as blood cells (e.g., peripheral blood cells, cord blood cells, and the like), mononuclear cell (e.g., lymphocyte (NK cells, B cells, T cells other than αβT cells (e.g., γδT cells and the like), monocyte, dendritic cell and the like)), granulocyte (e.g., eosinophils, neutrophil, basophil), megakaryocyte), epithelial cells, endothelial cells, muscle cells, fibroblasts (e.g., skin cells and the like), hair cells, hepatic cells, gastric mucosal cells, enterocytes, spleen cells, pancreatic cells (e.g., pancreatic exocrine cells and the like), brain cells, lung cells, kidney cells, and adipocytes. Among these, a mononuclear cell other than an αβT cell is preferable, more specifically, a monocyte or γδT cell is preferable.

As a method for introducing a reprogramming factor into a somatic cell when the reprogramming factor is in the form of a DNA, for example, calcium phosphate coprecipitation method, PEG method, electroporation method, microinjection method, lipofection method and the like can be used. For example, the methods described in Cell Engineering additional volume 8, New Cell Engineering experiment protocol, 263-267 (1995) (published by Shujunsha), Virology, vol. 52, 456 (1973), Folia Pharmacol. Jpn., vol. 119 (No. 6), 345-351 (2002) and the like can be used. When a virus vector is used, the nucleic acid is introduced into a suitable packaging cell (e.g., Plat-E cell) and complementation cell line (e.g., 293 cell), a virus vector produced in the culture supernatant is recovered, and cells are infected with the vector by an appropriate method suitable for each virus vector, whereby the vector is introduced into the cells. For example, when a retrovirus vector is used as the vector, a specific means is disclosed in WO 2007/69666, Cell, 126, 663-676 (2006) and Cell, 131, 861-872 (2007) and the like. Particularly, when a retrovirus vector is used, highly efficient transfection into various cells is possible by using a recombinant fibronectin fragment CH-296 (manufactured by Takara Bio Inc.).

A reprogramming factor in the form of RNA may be directly introduced into cells and expressed in the cells. As a method for introducing RNA, a known method can be used and, for example, a lipofection method, an electroporation method, or the like can be preferably used. When the reprogramming factor is in the form of a protein, it can be introduced into a cell by a method such as lipofection, fusion with cellular membrane-penetrating peptide (e.g., HIV-derived TAT and polyarginine), microinjection and the like, and the like.

Examples of the basal medium include, but are not limited to, Dulbecco's Medium (e.g., IMDM), Eagle's medium (e.g., DMEM, EMEM, BME, MEM, αMEM), Ham's medium (e.g., F10 medium, F12 medium), RPMI medium (e.g., RPMI-1640 medium, RPMI-1630 medium), MCDB medium (e.g., MCDB104, 107, 131, 151, 153 medium), Fischer's medium, 199 medium, culture medium for primate ES cell (culture medium for primate ES/iPS cell, Reprocell), medium for mouse ES cell (TX-WES culture medium, Thromb-X), serum-free medium (mTeSR, Stemcell Technologies), ReproFF, StemSpan (registered trade mark) SFEM, StemSpan (registered trade mark) H3000, StemlineTI, ESF-B medium, ESF-C medium, CSTI-7 medium, Neurobasal medium (Life Technologies), StemPro-34 medium, StemFit (registered trade mark) (e.g., StemFit AK03N, StemFit AK02N) and the like. Furthermore, these media can be mixed as necessary and used and, for example, DMEM/F12 medium and the like can be mentioned.

The basal medium may be appropriately supplemented with 10%-20% serum (fetal bovine serum (FBS), human serum, horse serum) or a serum replacement (KSR and the like), insulin, various vitamins, L-glutamine, various amino acids such as non-essential amino acid and the like, 2-mercaptoethanol, various cytokines (interleukins (IL-2, IL-7, IL-15 etc.), SCF (Stem cell factor), activin and the like), various hormones, various growth factors (Leukemia inhibitory factor (LIF), basic fibroblast growth factor (bFGF), TGF-β etc.), various extracellular matrices, various cell adhesion molecules, antibiotics such as penicillin/streptomycin, puromycin and the like, pH indicator such as phenol red and the like, and the like.

Culturing is preferably performed, for example, under 1%-10%, preferably 2%-5%, $CO_2$ atmosphere at, for example, about 37° C.-42° C., preferably about 37° C.-39° C., for about 25-50 days.

In the present invention, a mammal from which a somatic cell is taken is not particularly limited, and is preferably human. Autologous cells, allogeneic cells having the same or substantially the same HLA type, allogeneic cells in which the presence or absence of the expression and/or expression level of HLA are/is adjusted and the like are preferable since rejections do not occur. As HLA, the presence or absence of the expression and/or expression level of at least a part of the subunits contained in class I and/or class II is preferably adjusted.

(2) Step for Differentiating Induced Pluripotent Stem Cells into T Cells

A method for differentiating induced pluripotent stem cells into T cells is not particularly limited as long as induced pluripotent stem cells can be differentiated into γδT cells. In one embodiment of the present invention, the step for differentiating induced pluripotent stem cells into T cells may contain (2-1) a step for differentiating induced pluripotent stem cells into hematopoietic progenitor cells, and (2-2) a step for differentiating the hematopoietic progenitor cells into CD3 positive T cells.

(2-1) Step for Differentiating Induced Pluripotent Stem Cells into Hematopoietic Progenitor Cells In the present invention, the "hematopoietic progenitor cell(s) (HPC)" means CD34 positive cell, preferably, CD34/CD43 double positive (DP) cell. In the present invention, hematopoietic progenitor cell and hematopoietic stem cell are not distinguished and show the same cell unless particularly indicated.

The method of differentiating induced pluripotent stem cells into hematopoietic progenitor cells is not particularly limited as long as it can cause differentiation into hematopoietic progenitor cells. Examples thereof include a method including culturing pluripotent stem cells in a medium for induction of hematopoietic progenitor cells, as described in, for example, WO 2013/075222, WO 2016/076415 and Liu S. et al., Cytotherapy, 17 (2015); 344-358 and the like.

In the present invention, a medium used for induction into a hematopoietic progenitor cell is not particularly limited. A medium used for culturing animal cells can be prepared into a basal medium. The basal medium may be similar to those used in the above-mentioned step (1). The medium may contain serum or may be serum-free. If necessary, the basal medium may also contain Vitamin C (e.g., ascorbic acid), albumin, insulin, transferrin, selenium compound (e.g., sodium selenite), fatty acid, trace elements, 2-mercaptoethanol, thioglycerol (e.g., α-monothioglycerol (MTG)), lipids, amino acids, L-glutamine, L-alanyl-L-glutamine (e.g., Glutamax (registered trade mark)), non-essential amino acids, vitamins, growth factors, low-molecular-weight compounds, antibiotics (e.g., penicillin, streptomycin), antioxidants, pyruvic acid, buffers, inorganic salts, cytokines, and the like.

In the present invention, "Vitamin C" means L-ascorbic acid and derivatives thereof, and "L-ascorbic acid derivative" means derivatives that become vitamin C by enzymatic reaction in the living body. Examples of the derivatives of L-ascorbic acid include vitamin C phosphate (e.g., ascorbic acid 2-phosphate), ascorbic acid glucoside, ascorbyl ethyl, vitamin C ester, ascorbyl tetrahexyldecanoate, ascorbyl stearate, and ascorbyl 2-phosphate 6-palmitate. Preferred is vitamin C phosphate (e.g., ascorbic acid 2-phosphate), and examples of the vitamin C phosphate include salts of L-ascorbic acid phosphate such as L-ascorbic acid phosphate Na and L-ascorbic acid phosphate Mg.

When Vitamin C is used, the Vitamin C is preferably added (supplied) every four days, every three days, every two days, or every day. The Vitamin C is more preferably added every day. In one embodiment, Vitamin C is added to the medium at an amount corresponding to 5 ng/ml to 500 ng/ml (e.g., an amount corresponding to 5 ng/ml, 10 ng/ml, 25 ng/ml, 50 ng/ml, 100 ng/ml, 200 ng/ml, 300 ng/ml, 400 ng/ml, or 500 ng/ml). In another embodiment, Vitamin C is added to the culture medium at an amount corresponding to 5 µg/ml-500 µg/ml (e.g., an amount corresponding to 5 µg/ml, 10 µg/ml, 25 µg/ml, 50 µg/ml, 100 µg/ml, 200 µg/ml, 300 µg/ml, 400 µg/ml, 500 µg/ml).

The medium to be used in step (2-1) may be further supplemented with at least one kind of cytokine selected from the group consisting of BMP4 (Bone morphogenetic protein 4), VEGF (vascular endothelial growth factor), SCF (Stem cell factor), TPO (thrombopoietin), FLT-3L (Flt3 Ligand) and bFGF (basic fibroblast growth factor). It is more preferably a culture supplemented with BMP4, VEGF and bFGF, and further preferably a culture supplemented with BMP4, VEGF, SCF and bFGF.

When cytokine is used, its concentration in the medium may be, for example, 5 ng/ml-500 ng/ml for BMP4, 5 ng/ml-500 ng/ml for VEGF, 5 ng/ml-100 ng/ml for SCF, 1 ng/ml-100 ng/ml for TPO, 1 ng/ml-100 ng/ml for FLT-3L, and 5 ng/ml-500 ng/ml for bFGF.

The aforementioned medium may be supplemented with a TGFβ inhibitor. The TGFβ inhibitor is a small molecule inhibitor that interferes with the signal transduction of TGFβ family and includes, for example, SB431542, SB202190 (both R. K. Lindemann et al., Mol. Cancer 2:20 (2003)), SB505124 (GlaxoSmithKline), NPC30345, SD093, SD908, SD208 (Scios), LY2109761, LY364947, LY580276 (Lilly Research Laboratories) and the like. For example, when the TGFβ inhibitor is SB431542, its concentration in the medium is preferably 0.5 µM-100 µM.

The induced pluripotent stem cells may be cultured by adherent culture or suspension culture. In cases of adherent culture, the culturing may be carried out in a culture vessel coated with an extracellular matrix component, and may be co-cultured with feeder cells. While the feeder cell is not particularly limited, for example, fibroblast (mouse embryo fibroblast (MEF), mouse fibroblast (STO) and the like) can be mentioned. Feeder cells are preferably inactivated by a method known per se, for example, radiation (gamma-ray and the like) irradiation, treatment with anti-cancer agent (mitomycin C and the like) and the like. As the extracellular matrix component, fibrous proteins such as Matrigel (Niwa A, et al. PLoS One.6(7):e22261, 2011), gelatin, collagen, elastin and the like, glucosaminoglycan and proteoglycan such as hyaluronic acid, chondroitin sulfate and the like, cell adhesion proteins such as fibronectin, vitronectin, laminin and the like, and the like can be mentioned.

Suspension culture means culturing cells in a state of non-adhesion to a culture container and is not particularly limited. To improve adhesiveness to the cells, a culture container free of an artificial treatment (e.g., coating treatment with extracellular matrix and the like), or a culture container subjected to a treatment for artificially suppressing adhesion (e.g., coating treatment with polyhydroxyethyl methacrylic acid (poly-HEMA) or non-ionic surface active polyol (Pluronic F-127 etc.)) can be used. In the suspension culture, embryoid (EB) is preferably formed and cultured.

In the present invention, hematopoietic progenitor cell can also be prepared from a sac-like structure (to be also referred to as ES-sac or iPS-sac) obtained by culturing pluripotent stem cells. As used herein, the "sac-like structure" is a pluripotent stem cell-derived three-dimensional saccular (with spaces inside) structure, which is formed by an endothelial cell population and the like and contains hematopoietic progenitor cells in the inside thereof.

The temperature conditions are not particularly limited. The temperature is, for example, about 37° C. to about 42° C., preferably about 37° C. to about 39° C. The culture period may be appropriately determined by those skilled in the art by monitoring of the number of hematopoietic progenitor cells and/or the like. The number of days of the culture is not limited as long as hematopoietic progenitor cells can be obtained. Examples of the culture period include at least 6 days, not less than 7 days, not less than 8 days, not less than 9 days, not less than 10 days, not less than 11 days, not less than 12 days, not less than 13 days, and not less than 14 days. The culture period is preferably 14 days. While a longer culture period generally does not pose a problem in the production of hematopoietic progenitor cells, it is preferably not more than 35 days, more preferably not more than 21 days. The culture may be carried out under low-oxygen conditions, and the low-oxygen condition in the present invention means, for example, oxygen concentration of 15%, 10%, 9%, 8%, 7%, 6%, 5% or lower than these.

(2-2) Step of Differentiating Hematopoietic Progenitor Cells into CD3 Positive T Cells A method for differentiating hematopoietic progenitor cells into CD3 positive T cells is not particularly limited as long as it can differentiate hematopoietic progenitor cells into CD3 positive T cells. Examples thereof include a method for culturing hematopoietic progenitor cells under the same culture conditions as those in a method of inducing T cells from hematopoietic progenitor cells, as described in WO 2016/076415, WO 2017/221975 and the like.

In the present invention, a medium for inducing differentiation into CD3 positive T cell is not particularly limited, and a medium used for culturing animal cells can be prepared into a basal medium. Examples of the basal medium include those similar to the basal medium used in the above-mentioned step (1). The medium may contain serum, or may be serum-free. If necessary, the basal medium may also contain Vitamin C (e.g., ascorbic acid), albumin, insulin, transferrin, selenium compound (e.g., sodium selenite), fatty acid, trace elements, 2-mercaptoethanol, thioglycerol (e.g., α-monothioglycerol (MTG)), lipids, amino acids, L-glutamine, L-alanyl-L-glutamine (e.g., Glutamax (registered trade mark)), non-essential amino acids, vitamins, growth factors, low-molecular-weight compounds, antibiotics (e.g., penicillin, streptomycin), antioxidants, pyruvic acid, buffers, inorganic salts, cytokines, and the like.

When Vitamin C is used in step (2-2), Vitamin C may be the same as that described in step (2-1) and can be added similarly. In one embodiment, the concentration of Vitamin C in the medium or a culture medium is preferably 5 μg/ml-200 μg/ml. In another embodiment, vitamin C is added to the culture medium at an amount corresponding to 5 g/ml-500 μg/ml (e.g., amount corresponding to 5 μg/ml, 10 μg/ml, 25 μg/ml, 50 μg/ml, 100 μg/ml, 200 μg/ml, 300 μg/ml, 400 μg/ml, 500 μg/ml).

In step (2-2), p38 inhibitor and/or SDF-1 (Stromal cell-derived factor 1) are/is preferable. In the present invention, the "p38 inhibitor" means a substance that inhibits the functions of p38 protein (p38 MAP kinase). Examples thereof include, but are not limited to, chemical inhibitor of p38, dominant-negative mutant of p38 or nucleic acid encoding same and the like.

Examples of the chemical inhibitor of p38 to be used in the present invention include, but are not limited to, SB203580 (4-(4-fluorophenyl)-2-(4-methylsulfonylphenyl)-5-(4-pyridyl)-1H-imidazole), and a derivative thereof, SB202190 (4-(4-fluorophenyl)-2-(4-hydroxyphenyl)-5-(4-pyridyl)-1H-imidazole) and a derivative thereof, SB239063 (trans-4-[4-(4-fluorophenyl)-5-(2-methoxy-4-pyrimidinyl)-1H-imidazol-1-yl]cyclohexanol) and a derivative thereof, SB220025 and a derivative thereof, PD169316, RPR200765A, AMG-548, BIRB-796, SClO-469, SCIO-323, VX-702 and FR167653. These compounds are commercially available and, for example, SB203580, SB202190, SC239063, SB220025 and PD169316 are available from Calbiochem, and SClO-469 and SCIO-323 are available from Scios and the like. The chemical inhibitor of p38 is preferably SB203580 (4-(4-fluorophenyl)-2-(4-methylsulfonylphenyl)-5-(4-pyridyl)-1H-imidazole), or a derivative thereof.

Examples of the dominant-negative mutant of p38 to be used in the present invention include p38T180A obtained by point mutation of the 180-position threonine located in the DNA binding region of p38 to alanine, p38Y182F obtained by point mutation of the 182-position tyrosine of p38 in human and mouse 20 to phenylalanine and the like. The p38 inhibitor is contained in a medium at about 1 μM-about 50 μM. When SB203580 is used as the P38 inhibitor, it may be contained in a medium at 1 μM-50 M, 5 μM-30 μM, 10 μM-20 μM.

SDF-1 to be used in the present invention may be not only SDF-1α or a mature form thereof, but also an isoform such as SDF-1β, SDF-1γ, SDF-1δ, SDF-1ε, SDF-1φ and the like or a mature form thereof, or a mixture of these at any ratio or the like. Preferably, SDF-1α is used. SDF-1 is sometimes referred to as CXCL-12 or PBSF.

In the present invention, one or several amino acids in the amino acid sequence of SDF-1 may be substituted, deleted, added and/or inserted as long as it has the activity as the chemokine (SDF-1 with such substitution, deletion, addition and/or insertion of amino acid is to be also referred to as "SDF-1 mutant"). Similarly, sugar chain may be substituted, deleted and/or added in SDF-1 or SDF-1 mutant. Examples of the mutant of the above-mentioned SDF-1 include those maintaining at least 4 cysteine residues (Cys30, Cys32, Cys55 and Cys71 in human SDF-1α) and having not less than 90% identity with amino acid sequence of a natural substance, though the amino acid mutation is not limited thereto. SDF-1 may be obtained from a mammal, for example, human or non-human mammal such as monkey, sheep, bovine, horse, swine, dog, cat, rabbit, rat, mouse and the like. For example, the protein registered as GenBank accession number:NP_954637 can be used as human SDF-1α, and the protein registered as GenBank accession number:NP_000600 can be used as SDF-1β.

SDF-1 may be commercially available, purified from nature, or produced by peptide synthesis or genetic engineering techniques. SDF-1 is contained in a medium within the range of, for example, about 10 ng/ml to about 100 ng/ml. In addition, SDF-1 alternative having an SDF-1-like activity can also be used instead of SDF-1. Examples of such SDF-1 alternative include CXCR4 agonist, and a low-molecular-weight compound having a CXCR4 agonist activity and the like may be added to the medium instead of SDF-1.

The culture medium used in step (2-2) may be further supplemented with at least one kind, preferably all, of cytokine selected from the group consisting of SCF, TPO (thrombopoietin), FLT-3L and IL-7. The concentration of these is, for example, 10 ng/ml to 100 ng/ml for SCF, 10 ng/ml to 200 ng/ml for TPO, 1 ng/ml to 100 ng/ml for IL-7, and 1 ng/ml to 100 ng/ml for FLT-3L.

In step (2-2), the hematopoietic progenitor cells may be cultured by adherent culture or suspension culture. In cases of adherent culture, a coated culture vessel may be used. The hematopoietic progenitor cells may be co-cultured with feeder cells and/or the like. Examples of the feeder cells for the co-culture include a bone-marrow stromal cell line, OP9 cells (available from Riken BioResource Center). The OP9 cell is preferably OP9-DL4 cell or OP9-DL1 cell, which constantly expresses DLL4 or DLL1 (e.g., Holmes R I and Zuniga-Pflucker J C. Cold Spring Harb Protoc. 2009(2)). In the present invention, in cases where OP9 cells are used as the feeder cells, separately-prepared DLL1 or DLL4, or a fusion protein of DLL4 or DLL1, and Fc or the like, may be added to the medium to perform the co-culture. When feeder cells are used, the feeder cells are preferably appropriately replaced during the culture. The replacement of the feeder cells may be carried out by transferring the subject cells that are being cultured onto feeder cells that are preliminarily plated. The replacement may be carried out every five days, every four days, every three days, or every two days. When hematopoietic progenitor cells are obtained by suspension culture of embryoid, it is preferable to perform adhesion culture after dissociation into single cells. While the cells may be co-cultured with feeder cells, culturing is preferably carried out without using feeder cells.

In the case of adhesion culture and when a culture container is coated, examples of the coating agent include Matrigel (Niwa A, et al. PLos One, 6(7):e22261, 2011)), collagen, gelatin, laminin, heparan sulfuric acid proteoglycan, RetroNectin (registered trade mark), fusion protein of DLL4 or DLL1, or DLL4 or DLL1, and Fc region of antibody (hereinafter sometimes referred to as Fc) and the like (e.g., DLL4/Fc chimera), entactin, and/or combination of these, and a combination of RetroNectin and fusion protein of DLL4 and Fc etc. is preferable.

In step (2-2), the culture temperature conditions are not limited. The temperature is, for example, about 37° C. to about 42° C., preferably about 37° C. to about 39° C. The culture period may be appropriately determined by those skilled in the art by monitoring of the number of γδT cells and the like. The number of days of the culture is not limited as long as γδT cells can be obtained. Examples of the culture period include typically at least not less than 10 days, not less than 12 days, not less than 14 days, not less than 16 days, not less than 18 days, or not less than 20 days. The culture period is preferably 21 days. In addition, not more than 90 days is preferable, and not more than 42 days is more preferable.

The CD3 positive T cell population obtained by the above step include γδT cells. Step (2) may further contain the following step (2-3).

(2-3) Step for Concentrating CD3 Positive T Cells

A method for concentrating CD3 positive T cells is not particularly limited as long as γδT cells can be concentrated. For example, a method of culturing CD3 positive T cells under the same culture conditions as those in a step of inducing CD8 positive T cells from CD4CD8 double positive T cells, as described in WO 2016/076415, WO 2017/221975 and the like can be mentioned.

In the present invention, a medium used for concentrating CD3 positive T cells is not particularly limited, and a medium used for culturing animal cells can be prepared into a basal medium. Examples of the basal medium include those similar to the basal medium used in the above-mentioned step (1). The medium may contain serum, or may be serum-free. If necessary, the basal medium may also contain Vitamin C (e.g., ascorbic acid), albumin, insulin, transferrin, selenium compound (e.g., sodium selenite), fatty acid, trace elements, 2-mercaptoethanol, thioglycerol (e.g., α-monothioglycerol (MTG)), lipids, amino acids, L-glutamine, L-alanyl-L-glutamine (e.g., Glutamax (registered trade mark)), non-essential amino acids, vitamins, growth factors, low-molecular-weight compounds, antibiotics (e.g., penicillin, streptomycin), antioxidants, pyruvic acid, buffers, inorganic salts, cytokines, hormone, and the like. In one embodiment of the present invention, Vitamin C such as ascorbic acid and the like, insulin, transferrin, selenium compound (e.g., sodium selenite), cytokine such as IL-7 and the like may be contained.

When Vitamin C is used in step (2-3), Vitamin C may be the same as that described in step (2-1) and can be added similarly. In one embodiment, the concentration of Vitamin C in the medium or a culture medium is preferably 5 μg/ml-200 μg/ml. In another embodiment, vitamin C is added to the culture medium at an amount corresponding to 5 μg/ml-500 μg/ml (e.g., amount corresponding to 5 μg/ml, 10 μg/ml, 25 μg/ml, 50 μg/ml, 100 μg/ml, 200 μg/ml, 300 μg/ml, 400 μg/ml, 500 μg/ml).

When hormone is used in step (2-3), examples of the hormone include cortical hormone. Cortical hormone is glucocorticoid or a derivative thereof, and cortisone acetate, hydrocortisone, fludrocortisone acetate, prednisolone, triamcinolone, methylprednisolone, dexamethasone, betamethasone, and beclometasone dipropionate are recited as examples. Preferred is dexamethasone. When cortical hormone is dexamethasone, its concentration in the medium is 1 nM-100 nM.

In step (2-3), the medium contains a CD3/TCR complex agonist. The CD3/TCR complex agonist is not particularly limited as long as it is a molecule capable of transducing a signal from a CD3/TCR complex to a CD3 positive cell by specifically binding to the CD3/TCR complex. Examples of the CD3/TCR complex agonist include CD3 agonist and/or TCR agonist. As the CD3 agonist, an anti-CD3 agonist antibody (to be also simply referred to as "anti-CD3 antibody") or a binding fragment thereof can be mentioned, and as the TCR agonist, at least one selected from the group consisting of an anti-TCR agonist antibody (to be also simply referred to as "anti-TCR antibody") or a binding fragment thereof, an MHC/antigen peptide complex or a multimer thereof, and an MHC/superantigen complex or a multimer thereof can be mentioned. When an anti-CD3 antibody is used, the anti-CD3 antibody includes both a polyclonal antibody and a monoclonal antibody, preferably a monoclonal antibody. The antibody may belong to any immunoglobulin class of IgG, IgA, IgM, IgD and IgE, preferably IgG. As the anti-CD3 antibody, an antibody (OKT3) produced from OKT3 clone, an antibody (UCHT1) produced from UCHT1 clone and the like can be mentioned, preferably UCHT1. The concentration of anti-CD3 antibody in the medium is, for example, 10 ng/ml-1000 ng/ml, preferably 50 ng/ml-800 ng/ml, more preferably 250 ng/ml-600 ng/ml. The above-mentioned CD3/TCR complex agonist may be commercially available, purified from nature, or produced by peptide synthesis or genetic engineering techniques or chemical synthesis methods. For example, OKT3 and UCHT1 can be purchased from ThermoFisher, GeneTex and the like.

When cytokine is used in step (2-3), IL-2 and IL-7 and the like can be mentioned as the cytokine. When cytokine is IL-2, the concentration thereof in the medium is 10 U/ml-1000 U/mL, and when it is IL-7, the concentration thereof in the medium is 1 ng/ml-1000 ng/mL.

In step (2-3), the culture temperature conditions are not particularly limited. The temperature is, for example, about 37° C. to about 42° C., preferably about 37° C. to about 39° C. The culture period can be appropriately determined by those skilled in the art by monitoring the number of γδT cells and the like. The number of days is not limited as long as γδT cells can be obtained. The culture period is, for example, not less than 1 day, not less than 2 days, not less than 3 days, not less than 4 days, not less than 5 days, preferably not less than 6 days. It is preferably not more than 28 days, more preferably not more than 14 days.

The CD3 positive T cell population obtained by the above step include γδT cells, and may be further concentrated. Step (2) may further contain the following step (2-4).

(2-4) Step for Expansion Culture of CD3 Positive T Cells Containing γδT Cells

A method for expansion culture of CD3 positive T cells is not particularly limited as long as γδT cells can be proliferated. For example, a method of culturing CD3 positive T cells containing γδT cells under the same culture conditions as those in a step of expansion culture of CD8α+β+ cytotoxic T cells, as described in WO 2016/076415, WO 2018/135646 and the like can be mentioned.

In the present invention, a medium used for expansion culture of CD3 positive T cells containing γδT cells is not particularly limited. A medium used for culturing animal cells can be prepared into a basal medium. The basal medium may be similar to those used in the above-mentioned step (2-3). The medium may contain a serum, or may be serum-free. If necessary, the basal medium may also contain Vitamin C (e.g., ascorbic acid), albumin, insulin, transferrin, selenium (e.g., sodium selenite), fatty acid, trace elements, 2-mercaptoethanol, thiol glycerol (e.g., alpha-monothioglycerol (MTG)), lipids, amino acids, L-glutamine, L-alanyl-L-glutamine (e.g., Glutamax (registered trade mark)), non-essential amino acids, vitamins, growth factors, low-molecular-weight compounds, antibiotics (e.g., penicillin, streptomycin), antioxidants, pyruvic acid, buffers, inorganic salts, cytokines, hormone, and the like. In one embodiment of the present invention, vitamin C such as ascorbic acid and the like, insulin, transferrin, selenium compound (e.g., sodium selenite), cytokine such as IL-7 and the like may be contained.

When Vitamin C is used in step (2-4), Vitamin C may be the same as that described in step (2-1) and can be added similarly. In one embodiment, the concentration of Vitamin C in the medium or a culture medium is preferably 5 µg/ml-200 g/ml. In another embodiment, vitamin C is added to the culture medium at an amount corresponding to 5 µg/ml-500 µg/ml (e.g., amount corresponding to 5 µg/ml, 10 g/ml, 25 µg/ml, 50 µg/ml, 100 µg/ml, 200 µg/ml, 300 µg/ml, 400 µg/ml, 500 µg/ml).

In step (2-4), the medium contains a CD3/TCR complex agonist. The CD3/TCR complex agonist is not particularly limited as long as it is a molecule capable of transducing a signal from a CD3/TCR complex to a CD3 positive cell by specifically binding to the CD3/TCR complex. Examples of the CD3/TCR complex agonist include CD3 agonist and/or TCR agonist. As the CD3 agonist, an anti-CD3 agonist antibody (to be also simply referred to as "anti-CD3 antibody") or a binding fragment thereof can be mentioned, and as the TCR agonist, at least one selected from the group consisting of an anti-TCR agonist antibody (to be also simply referred to as "anti-TCR antibody") or a binding fragment thereof, an MHC/antigen peptide complex or a multimer thereof, and an MHC/superantigen complex or a multimer thereof can be mentioned. When an anti-CD3 antibody is used, the anti-CD3 antibody includes both a polyclonal antibody and a monoclonal antibody, preferably a monoclonal antibody. The antibody may belong to any immunoglobulin class of IgG, IgA, IgM, IgD and IgE, preferably IgG. As the anti-CD3 antibody, an antibody (OKT3) produced from OKT3 clone, an antibody (UCHT1) produced from UCHT1 clone and the like can be mentioned, preferably UCHT1. The concentration of anti-CD3 antibody in the medium is, for example, 0.3 ng/ml-10000 ng/ml, preferably 50 ng/ml-5000 ng/ml, more preferably 200 ng/ml-4000 ng/ml. The above-mentioned CD3/TCR complex agonist may be commercially available, purified from nature, or produced by peptide synthesis or genetic engineering techniques or chemical synthesis methods. For example, OKT3 and UCHT1 can be purchased from ThermoFisher, GeneTex and the like.

Fibronectin or a variant thereof is preferably present in the medium in step (2-4). Such fibronectin is not particularly limited as long as it is a molecule capable of binding to CD3 positive cells. The variant of fibronectin is not particularly limited as long as it is a molecule capable of binding to VLA-5 and VLA-4 on the surface of CD3 positive cells, and examples thereof include RetroNectin. Fibronectin and a variant thereof may be present in any form in the medium. For example, they may be contained in the medium during culture, or may be immobilized on a culture container, and are preferably immobilized on a culture container.

When fibronectin or a variant thereof is contained in a medium, the medium may be the same as that containing a CD3/TCR complex agonist. The presence or absence of serum, additive and the like may be the same as that in the medium containing a CD3/TCR complex agonist. When fibronectin or a variant thereof is contained in a medium, the lower limit of the concentration of fibronectin or a variant thereof may be not less than 10 ng/ml, preferably not less than 100 ng/ml, and the upper limit may be not more than 10000 µg/ml, preferably not more than 1000 µg/ml.

In step (2-4), the medium also preferably contains a CD30 agonist. The CD30 agonist is not particularly limited as long as it is a molecule capable of transducing a signal from a CD30 into a cell by specifically binding to CD30. Examples of the CD30 agonist include at least one selected from the group consisting of anti-CD30 agonist antibody (to be also simply referred to as "anti-CD30 antibody") or a binding fragment thereof and CD30 ligand or a binding fragment thereof.

Like the CD3/TCR complex agonist, the CD30 agonist used in step (2-4) may be present in any form as long as it can be present in contact with CD30 during culturing. For example, it may be contained in the medium during culture, or may be immobilized on a culture container, and is preferably contained in the medium.

When a CD30 agonist is contained in a medium, the medium may be the same as that containing a CD3/TCR complex agonist. The presence or absence of serum, additive and the like may be the same as that in the medium containing a CD3/TCR complex agonist. When a CD30 agonist is contained in a medium, the concentration of the CD30 agonist in the medium can be appropriately determined by those of ordinary skill in the art according to the CD30 agonist. For example, when the CD30 agonist is an anti-CD30 agonist antibody or a binding fragment thereof, the concentration of the anti-CD30 agonist antibody or a binding fragment thereof in the medium is generally 1 ng/ml-10000 ng/ml, preferably 30 ng/ml-300 ng/ml.

When the CD30 agonist is immobilized on a culture container, the culture container may be the same as that on which the CD3/TCR complex agonist is immobilized. In addition, a method of immobilizing the CD30 agonist on the culture container may be the same as that of immobilizing the CD3/TCR complex agonist. The lower limit of the concentration of a CD30 agonist solution when the CD30 agonist is immobilized on a culture container may be not less than 0.1 ng/ml, preferably not less than 1 ng/ml, and the upper limit may be not more than 10000 ng/ml, preferably not more than 1000 ng/ml.

When cytokine is used in step (2-4), cytokine may be IL-2, IL-7, IL-12, IL-15, IL-18, IL-21 or the like. Only one kind of these may be used or plural kinds (preferably all kinds) thereof may be used. When cytokine is IL-2, the concentration thereof in the medium may be 10 U/ml-1000 U/ml, when cytokine is IL-7, the concentration thereof in the medium may be 1 ng/ml-1000 ng/ml. The concentration of IL-12 in the medium may be 5 ng/ml-500 ng/ml, the concentration of IL-15 in the medium may be 1 ng/ml-100 ng/ml, the concentration of IL-18 in the medium may be 5 ng/ml-500 ng/ml, and the concentration of IL-21 in the medium may be 2 ng/ml-200 ng/ml.

In step (2-4), a TNF family cytokine may be contained as cytokine in the medium. Examples of the TNF family cytokine include TNF-α, TNF-β, lymphotoxin α, Fas ligand, TRAIL, TWEAK, TL1A, RANK ligand, OX40 ligand, APRIL, AITRL, BAFF, 4-1BBL and CD40 ligand and the like, and TL1A is preferable. When TL1A is used, the concentration thereof in the medium may be 5 ng/ml-500 ng/ml, preferably 10 ng/ml-300 ng/ml, more preferably 20 ng/ml-200 ng/ml.

In step (2-4), moreover, an apoptosis inhibitor may be further contained in the medium. As the apoptosis inhibitor, a protease inhibitor can be mentioned, for example, caspase inhibitor. As the caspase inhibitor, Pan Caspase FMK inhibitor Z-VAD (N-benzyloxycarbonyl-Val-Ala-Asp(0-Me) fluoromethylketone) (hereinafter sometimes referred to as "Z-VAD-FMK") is preferable, and the concentration thereof in the medium may be 1 µM-1000 M, preferably 1 µM-500 µM, more preferably 1 µM-200 µM, particularly preferably 1 µM-50 M.

In the present invention, the obtained γδT cells may be used after isolation, or may be used as it is (namely, as a cell population possibly containing other cell type). When isolated, isolation can be performed using at least one molecule selected from the group consisting of γTCR, δTCR and CD3 as an index, and the isolation method used may be a method well known to those of ordinary skill in the art. Examples thereof include, but are not limited to, a method using an antibody of γTCR, δTCR and CD3 (bound with magnetic beads and the like as necessary) and isolation by flow cytometry or magnetic cell separation method, a purification method using an affinity column on which a desired antigen is immobilized and the like.

When used as it is, the ratio of the γδT cells in the cell population may be increased by using a method well known to those of ordinary skill in the art. Examples of the method for increasing the ratio of the γδT cells in the cell population include, but are not limited to, the methods of Front. Immunol., 5:636 (2014), National Publication of International Patent Application No. 2017-537625, National Publication of International Patent Application No. 2003-529363 and the like.

The cells used for the production method of the present invention optionally have a nucleic acid encoding an exogenous TCR and/or a chimeric antigen receptor (CAR), each of which recognizes and binds to an antigen or an antigen-HLA complex. Therefore, one embodiment of the present invention may include a step for introducing a nucleic acid encoding the aforementioned TCR (i.e., (i) αTCR and TCR, (ii) γTCR and δTCR), and/or a nucleic acid encoding (iii) the aforementioned CAR into the cell (e.g., pluripotent stem cell, hematopoietic progenitor cell etc.) obtained in any time of (1) a step for establishing an induced pluripotent stem cell from a cell other than an αβT cell, and (2) a step for differentiating the induced pluripotent stem cell established in step (1) into T cells. Of these, the nucleic acid encoding (i) αTCR and βTCR is introduced into γδT cells obtained during any of the steps of differentiating induced pluripotent stem cells into T cells. In the present specification, the nucleic acid encoding TCR means a nucleic acid containing a base sequence encoding one strand forming TCR and a base sequence encoding the other strand. The nucleic acid encoding TCR also means a combination of a nucleic acid containing a base sequence encoding one strand forming TCR and a nucleic acid containing a base sequence encoding the other strand. That is, when a nucleic acid encoding TCR ((i) αTCR and βTCR) is introduced into a cell, one nucleic acid containing both the base sequence encoding αTCR and the base sequence encoding βTCR may be introduced, or the base sequence encoding αTCR and the base sequence encoding @TCR may be introduced separately. When introduced separately, these nucleic acids may be introduced simultaneously or sequentially. The same applies to (ii) γTCR and δTCR.

The TCR used in the present invention encompasses not only one in which β chain and β chain of TCR constitute a heterodimer (i.e., αTCR), or γ chain and δ chain of TCR constitute a heterodimer (i.e., γδTCR), but also one in which they constitute a homodimer. Furthermore, one lacking a part of or whole constant region and one with recombination of an amino acid sequence may also be used. Of these, γδTCR is preferable, and Vγ9VΩTCR is particularly preferable.

The constant region of the above-mentioned TCR chain may be the constant region of the TCR chain of the cytotoxic T lymphocyte (CTL) clone, from which it is derived, wherein the region has been subjected to a predetermined modification. Examples of the modification include, but are not limited to, replacing particular amino acid residues in the constant region of the TCR of the CTL clone with cysteine residues, thereby enhancing efficiency of dimer expression by disulfide bond between TCR chains and the like.

Examples of the antigen targeted by the above-mentioned TCR include, but are not limited to, tumor antigens. The tumor antigen may be a tumor-specific antigen (TSA) or a tumor-associated antigen (TAA). Specific examples of such tumor antigen include one or more kinds of antigens selected from the group consisting of differentiated antigens such as MART-1/MelanA (MART-I), gp100 (Pmel 17), tyrosinase, TRP-1, TRP-2 and the like, tumor-specific multilineage antigens such as WT1, Glypican-3, MAGE-1, MAGE-3, BAGE, GAGE-1, GAGE-2, p15 and the like, fetal antigens such as CEA and the like, overexpressed tumor genes or mutated tumor suppressive genes such as p53, Ras, HER-2/neu and the like, unique tumor antigens caused by chromosome translocation such as BCR-ABL, E2A-PRL, H4-RET, IGH-IGK, MYL-RAR and the like, and virus antigens such as Epstein Barr virus antigen EBVA, human papilloma virus (HPV) antigens E6 and E7 and the like. As other tumor antigens, TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, β-catenin, CDK4, Mum-1, p 15, p 16, 43-9F, 5T4, 791Tgp72, α-fetoprotein, β-HCG, BCA225, BTAA, CA 125, CA 15-3/CA 27.29/BCAA, CA 195, CA 242, CA-50, CAM43, CD68/P1, CO-029, FGF-5, G250, Ga733/EpCAM, HTgp-175, M344, MA-50, MG7-Ag, MOV18, NB/70K, NY-CO-1, RCAS1, SDCCAG16, TA-90/Mac-2 binding protein/cyclophilin C-associated protein, TAAL6, TAG72, TLP and TPS can be mentioned.

As shown in the Example described below, in one embodiment, among the γδT cells obtained by the production method of the present invention, the cells expressing chimeric antigen receptor (CAR) showed cytotoxic activity specific to the cells expressing the target antigen of the CAR and antitumor activity (to be also referred simply to as "cytotoxic activity" in the present specification). Therefore, from the aspect of antigen specific cytotoxic activity, the γδT cells obtained by the production method of the present invention preferably express CAR. Whether a cell has cytotoxic activity can be confirmed by a known method, and a preferred method includes, for example, a method for measuring cytotoxic activity against cells expressing the target antigen of CAR by a chromium release assay or the like.

In the present invention, the "chimeric antigen receptor (CAR)" means a fusion protein containing an antigen-binding domain, a transmembrane domain, and an intracellular signal transduction domain. The antigen-binding domain of CAR includes a short chain antibody (scFv) in which the light chain (VL) and heavy chain (VH) of the variable region of the antibody are linked in tandem via a spacer such as a linker (e.g., linker composed of G and S (GS linker) (for example, GGGS, GGGGS or a linker combining these (e.g., SEQ ID NO: 4 or 5, etc.) and the like)). The γβT cells expressing CAR recognize the antigen in the scFV region and then transduce the recognition signal thereof into T cells through the intracellular signal transduction domain. Introduction of CAR into the γδT cells makes it possible to impart specificity to the antigen of interest. In addition, since CAR can directly recognize antigen molecules without depending on HLA class I or class II, a high immune response can also be induced against cells with decreased HLA class I or class II gene expression. As the antigen targeted by the aforementioned CAR, the same antigens as the above-mentioned antigens targeted by the aforementioned TCR can be mentioned.

Examples of the transmembrane domain of CAR include, but are not limited to, transmembrane domains derived from one or more proteins selected from the group consisting of α chain, β chain or ζ chain of TCR, CD28, CD3ε chain, CD45, CD4, CD5, CD8, CD9, CD16, CD22, CD33, CD37, CD64, CD80, CD86, CD134, 4-1BB(CD137) and CD154 and the like. The transmembrane domain of the molecule from which the first intracellular signal transduction domain linked to the antigen binding domain is derived may be used. For example, when the molecule from which the first intracellular signal transduction domain linked to the antigen binding domain is derived is CD28, the transmembrane domain may also be derived from CD28. Alternatively, an artificially designed transmembrane domain may also be used.

Examples of the intracellular signal transduction domain of CAR include, but are not limited to, intracellular domains derived from one or more proteins selected from the group consisting of CD3ζ chain (TCRζ chain), FcRγ chain, FcRβ chain, CD3γ chain, CD3δ chain, CD3ε chain, CD5, CD22, CD79a, CD79b and CD66d. Of these, an intracellular signal transduction domain derived from CD3ζ chain is preferable. The intracellular signal transduction domain may further contain an intracellular domain of a co-stimulatory molecule. Examples of the co-stimulatory molecule include intracellular domains of one or more kinds of proteins selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3 and CD83. The strength and duration of CAR activity can be controlled by selecting the type and number of co-stimulatory molecule to be bound (e.g., Mol Ther. 2009; 17:1453-1464.).

A spacer may be incorporated between the antigen-binding domain and transmembrane domain of CAR or between the intracellular transduction domain and transmembrane domain of CAR. As the spacer, a peptide generally consisting of not more than 300 amino acids, preferably 10-100 amino acids, most preferably 25-50 amino acids, can be used. Specific examples thereof include, but are not limited to, peptides containing a hinge region derived from IgG1, and CH2CH3 region of immunoglobulin and a part of CD3 and the like.

Examples of specific CAR include, but are not limited to, a first generation CAR in which scFv and CD3ζ chain are linked via a spacer, a second generation CAR in which a transmembrane domain derived from CD28 and an intracellular domain are incorporated between the scFV and CD3ζ chain of the first generation CAR to enhance the ability to activate T cells, and a third generation CAR in which the intracellular domain of a co-stimulatory molecule (4-1BB or OX40) different from CD28 is incorporated between the intracellular domain of CD28 and CD3ζ chain of the second generation.

More specific examples of CAR used in the present invention include a chimeric antigen receptor containing scFv recognizing CD19 as an antigen binding domain, transmembrane domain of CD8 as a transmembrane domain, intracellular domain derived from CD28 as an intracellular signal transduction domain, an intracellular domain derived from CD30, an intracellular domain derived from 4-1BB, and an intracellular domain derived from CD3ζ chain. The order of the above-mentioned intracellular domains contained in the intracellular signal transduction domain is not particularly limited and, for example, the order of the intracellular domain derived from CD28, the intracellular domain derived from CD30 or the intracellular domain derived from 4-1BB, and the intracellular domain derived from CD3ζ chain is adopted. More specifically, the chimeric antigen receptor in the present invention is composed of, for example, the amino acid sequence shown in SEQ ID NO: 1 or 2, or an amino acid sequence obtained by substitution, deletion, addition and/or insertion of one or two or more (preferably, about 1-100, preferably about 1-50, further preferably about 1-10, particularly preferably 1-several (2, 3, 4 or 5)) amino acids in the amino acid sequence shown in SEQ ID NO: 1 or 2.

Examples of the intracellular domain derived from CD30 include an amino acid sequence obtained by substitution, deletion, addition and/or insertion of one or two or more (preferably, about 1-100, preferably about 1-50, further preferably about 1-10, particularly preferably 1-several (2, 3, 4 or 5)) amino acids in the amino acid sequence shown in SEQ ID NO: 3. When the amino acid sequence is substituted, deleted, added and/or inserted as described above, the location of the substitution, deletion, addition and/or insertion is not particularly limited as long as the function of the intracellular domain of CD30 is maintained.

It can be confirmed by a known method that the above-mentioned TCR and/or CAR (hereinafter sometimes to be abbreviated as "TCR etc.") specifically recognizes antigen and can bind thereto. A suitable method includes, for example, dextramer assay, ELISPOT assay and the like. By performing the ELISPOT assay, it can be confirmed that T cells expressing TCR on the cell surface recognize the target antigen by the TCR etc. and the signal thereof has been transmitted into the cells.

Furthermore, the present inventors found that cytotoxic activity increases in cells expressing a fusion protein containing IL-15 and IL-15Rα (hereinafter sometimes to be abbreviated as "IL-15/IL-15Rα") together with the above-mentioned CAR, as compared to the cells expressing CAR alone. Therefore, from the aspect of cytotoxic activity, γδT cells obtained by the production method of the present invention preferably express IL-15/IL-15Ra, and more preferably express the above-mentioned CAR. Therefore, to obtain γδT cells expressing IL-15/IL-15Ra, the production method of the present invention may include a step of introducing a nucleic acid encoding IL-15/IL-15Rα into the cells obtained in any of steps (1) and (2) of the above-mentioned 1. (e.g., CD3 positive T cells obtained in step (2-2), CD3 positive T cells concentrated in step (2-3), and the like).

In the IL-15 signal transduction system, IL-15Rα expressed on antigen-presenting cells generally binds to IL-15 and IL-15 is presented to IL-15 receptor consisting of IL-15Rβ and a common γ chain (γc) on CD8-positive and CD4-negative cell (trans-presentation), whereby the cytotoxic activity of CD8 positive CD4 negative cell is maintained. Therefore, when the CD3 positive cell expressing IL-15/IL-15Rα is CD8 positive CD4 negative, the cell can transmit the IL-15 signal into its own cell via the IL-15 receptor. Alternatively, the CD3 positive cell expressing IL-15/IL-15Rα can transmit the IL-15 signal into other CD8 positive CD4 negative cells via the IL-15 receptor. As described above, since IL-15/IL-15Rα can maintain cytotoxic activity of CD8 positive CD4 negative cell, it is expected to show a continuous cytotoxic effect on cells targeted by CAR.

IL-15/IL-15Rα may be a transmembrane type protein or a secretor protein. It is known that, in IL-15Ra, the IL-15 binding domain of 1-65 amino acids from the N-terminal of the mature protein is the region responsible for binding to IL-15 (Wei X. et al., J. Immunol., 167: 277-282, 2001). Therefore, the transmembrane type protein may be a protein that retains the IL-15 binding domain and retains the transmembrane domain of IL-15Rα. On the other hand, the secretor protein may be a protein that maintains the IL-15 binding domain and lacks the transmembrane domain of IL-15Rα (e.g., protein consisting of 1-65 amino acid residues, 1-85 amino acid residues, or 1-182 amino acid residues of IL-15Rα, peptide containing an amino acid sequence not less than 85% identical with the amino acid sequence, and the like).

A spacer may be incorporated between IL-15 and IL-15Rα of IL-15/IL-15Rα. As the spacer, a peptide generally consisting of not more than 300 amino acids, preferably 10-100 amino acids, most preferably 20-50 amino acids, can be used. Specific examples thereof include, but are not limited to, the aforementioned GS linker and the like.

IL-15/IL-15Rα is not particularly limited as long as it is a protein in which IL-15 and IL-15Rα are fused, and specific examples thereof include a peptide consisting of SEQ ID NO: 6. While IL-15/IL-15Rα is not particularly limited as long as it can bind to the IL-15 receptor and transmit the IL-15 signal into the cell, for example, a peptide containing an amino acid sequence having a homology or identity of not less than about 90%, preferably not less than about 95%, more preferably not less than about 97%, particularly preferably not less than about 98%, most preferably not less than about 99%, with the amino acid sequence shown in SEQ ID NO: 6 can be mentioned. As used herein, the "homology" or "identity" means the proportion (%) of the same amino acid and similar amino acid residue (same amino acid residues in the case of identity) to all overlapping amino acid residues in the optimal alignment where two amino acid sequences are aligned using a mathematic algorithm known in the relevant technical field (preferably, the algorithm is such that a gap can be introduced into one or both of the sequences for the optimal alignment). The "similar amino acid" means amino acids having similar physicochemical properties and, for example, amino acids classified in the same group such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having a hydroxyl group (Ser, Thr), amino acids having a small side chain (Gly, Ala, Ser, Thr, Met) and the like can be mentioned. It is predicted that the substitution with such similar amino acids does not change the phenotype of the protein (that is, conservative amino acid substitution). Specific examples of the conservative amino acid substitution are well known in the technical field and are described in various documents (e.g., Bowie et al., Science, 247: 1306-1310 (1990)). The homology or identity of the amino acid sequence in the present specification can be calculated using homology calculation algorithm NCBI BLAST (National Center for Biotechnology Information Basic Local Alignment Search Tool), and under the following conditions (expectancy=10; accept gap; matrix=BLOSUM62; filtering=OFF).

The term "capable of binding" as used herein means "having an ability to bind" and refers to a capability to form a non-covalent complex with one or more other molecules. Various methods and assays to determine binding capability are known in the art. Binding is usually a binding with high affinity, wherein the affinity as measured in KD values preferably is less than 1 µM, more preferably less than 100 nM, even more preferably less than 10 nM, even more preferably less than 1 nM, even more preferably less than 100 µM, even more preferably less than 10 µM, even more preferably less than 1 µM. The term "KD" or "KD value" relates to the equilibrium dissociation constant as known in the art.

The above-mentioned TCR etc. are introduced into the cells in the form of a nucleic acid encoding TCR etc. In addition, a fusion protein containing IL-15 and IL-15R is also introduced into a cell in the form of a nucleic acid encoding the fusion protein. The nucleic acid may be DNA or RNA, or DNA/RNA chimera, and preferably DNA. In addition, the nucleic acid may be double-stranded or single-stranded. In the case of double strands, double-stranded DNA, double-stranded RNA or DNA:RNA hybrid may be used. When the nucleic acid is RNA, T is to be read as U as regards the RNA sequence. In addition, the nucleic acid may contain natural nucleotide, modified nucleotide, nucleotide analogue, or a mixture of these as long as it can express polypeptide in vitro or in a cell.

The above-mentioned nucleic acid can be constructed by a method known per se. For example, based on the amino acid sequence or nucleic acid sequence of known TCR or CAR, a DNA strand is chemically synthesized, or synthesized partially overlapping oligo DNA short chains are connected using PCR method or Gibson Assembly method, whereby a DNA encoding the full length or a part of the TCR or CAR can be constructed. The nucleic acid encoding a fusion protein containing IL-15 and IL-15Rα can also be constructed in the same manner.

The above-mentioned nucleic acid can be incorporated into an expression vector. The vector may be a vector that integrates or does not integrate into the genome of the target cell. In one embodiment the vector that does not integrate into the genome is capable of replicating outside the genome of the target cell. The vector may be present in multiple copies outside the genome of the target cell. In another embodiment of the invention, the vector integrates into the genome of the target cell. In preferable embodiments, the vector integrates at a pre-defined location of the genome of the target cell.

Examples of the promoter to be used in the above-mentioned vector include EF1α promoter, CAG promoter, SRα promoter, SV40 promoter, LTR promoter, CMV (cytomegalovirus) promoter, RSV (Rous sarcoma virus) promoter, MoMuLV (Moloney mouse leukemia virus) LTR, HSV-TK (simple herpes virus thymidine kinase) promoter, TCR V a gene promoter, TCR V gene promoter and the like. Of these, EF1α promoter, CAG promoter, MoMuLV LTR, CMV promoter, SRα promoter and the like are preferable.

The above-mentioned vector may contain transcription and translation regulatory sequence, ribosome binding site, enhancer, replication origin, polyA addition signal, selection marker gene and the like on demand besides the above-mentioned promoters. Examples of the selection marker gene include dihydrofolate reductase gene, neomycin resistance gene, puromycin resistance gene and the like.

In one embodiment of the present invention, heterodimers of α chain and β chain of TCR can be constructed in the target cell and on the cell surface by introducing an expression vector containing a nucleic acid encoding the α chain of TCR and a nucleic acid encoding β chain of TCR into the target cell. In this case, the nucleic acid encoding the α chain of TCR and the nucleic acid encoding β chain of TCR may be incorporated into separate expression vectors or a single expression vector. When they are incorporated into a single expression vector, these two kinds of nucleic acids are preferably incorporated via a sequence enabling polycistronic expression. Using a sequence enabling polycistronic expression, plural genes incorporated in one kind of expression vector can be more efficiently expressed. Examples of the sequence enabling polycistronic expression include 2A sequence (e.g., foot-and-mouth disease virus (FMDV)-derived 2A sequence (F2A), horse 25 rhinitis A virus (ERAV)-derived 2A sequence (E2A), Porcine teschovirus (PTV-1)-derived 2A sequence (P2A), Thosea asigna virus (TaV)-derived 2A sequence (T2A sequence) (PLoS ONE3, e2532, 2008, Stem Cells 25, 1707, 2007), internal ribosome entry site (IRES) (U.S. Pat. No. 4,937,190) and the like. From the aspect of uniform expression levels, P2A sequence and T2A sequence are preferable. The same applies to the case of using an expression vector containing a nucleic acid encoding the γ chain of TCR and a nucleic acid encoding the δ chain of TCR.

The above-mentioned expression vector is not particularly limited as long as it can express TCR etc. for a sufficient period of time for preventing or treating a disease when introduced into a cell. Examples thereof include viral vector, plasmid vector and the like. As the virus vector, retrovirus vector (including lentivirus vector and pseudo type vector), adenovirus vector, adeno-associated virus vector, herpes virus vector, Sendaivirus, episomal vector and the like can be mentioned. A transposon expression system (PiggyBac system) may also be used. As the plasmid vector, animal cell expression plasmid (e.g., pal-11, pXT1, pRc/CMV, pRc/RSV, pcDNAI/Neo) and the like can be mentioned.

There is no particular limitation on the method for introducing the above-mentioned nucleic acid or vector into cells, and known methods can be used. When nucleic acid and plasmid vector are introduced, a method similar to the method described in the step of the above-mentioned 1.(1) can be used. Alternatively, the above-mentioned nucleic acid may be introduced into the genome of the cell by genome editing (e.g., CRISPR system, TALEN, ZFN and the like).

The above-mentioned nucleic acid may also be directly introduced into cells in the form of RNA and used to express TCR etc. in the cells. As a method for introducing RNA, a known method can be used and, for example, a lipofection method, an electroporation method, or the like can be preferably used.

In the aforementioned steps (1) and (2), the timing of introduction of the above-mentioned nucleic acid is not particularly limited as long as TCR etc. introduced into the γδT cells can be expressed. For example, the nucleic acid can be introduced at the stage of iPS cell, HPC (CD34+/CD43+), ProT cells (CD4$^-$/CD8$^-$), CD3$^+$/CD4$^+$/CD8$^+$ T cells, CD3$^+$/CD4$^-$/CD8$^+$ T cells, or other cells (e.g., CD3$^-$/CD4$^+$/CD8$^+$ cells etc.).

When the above-mentioned nucleic acid is introduced into the cells, expression of endogenous TCR chain intrinsically expressed by the cells is preferably suppressed by siRNA in view of increased expression of the introduced TCR, suppression of emergence of mispaired TCR, and suppression of non-self-reactivity. When the aforementioned nucleic acid is applied to this method, to avoid the effect of siRNA on TCR, it is preferable that the base sequence of the nucleic acid encoding TCR is a sequence (codon conversion type sequence) different from the base sequence corresponding to the RNA acted on by the siRNA suppressing the expression of the endogenous TCR chain. These methods are described in, for example, WO 2008/153029. The aforementioned base sequence can be produced by introducing a silent mutation into a nucleic acid encoding TCR obtained naturally or chemically synthesizing artificially designed nucleic acid. To avoid mispairing with the endogenous TCR chain, a part or all of the constant regions of the nucleic acid encoding the introduced TCR may also be substituted with a constant region derived from an animal other than human, such as mouse.

2. γδT Cells or Cell Population Containing γδT Cells

The present invention also provides a γδT cell, or a cell population containing the γδT cells, wherein the γδT cell is a cell differentiated from an induced pluripotent stem cell derived from a cell other than an αβT cell. The ratio of the γδT cells contained in the above-mentioned cell population (number of γδT cells contained in the cell population/total number of cells contained in the cell population) is preferably not less than 90% (e.g., not less than 90%, not less than 95%, not less than 96%, not less than 97%, not less than 98%, not less than 99% or 100%). Such cell population can be obtained, for example, by the production method of the present invention. The ratio is calculated by measuring the proportion of cells expressing γTCR, δTCR and CD3 by flow cytometry. Therefore, in one embodiment, the present invention provides γδT cells produced by the production method of the present invention and/or a cell population containing the γδT cells. The aforementioned γδT cells may contain the nucleic acid encoding exogenous TCR, nucleic acid encoding CAR, and/or nucleic acid encoding a fusion protein containing IL-15 and IL-15Rα, which are described in the above-mentioned 1. In the following, the mentioned γδT cells or cell population containing the γδT cells is collectively referred to as "the cell etc. of the present invention".

3. Medicament Containing the Cell Etc. of the Present Invention

The present invention provides a medicament containing the cell etc. of the present invention as an active ingredient (hereinafter sometimes to be referred to as "the medicament of the present invention"). The cell etc. of the present invention may exhibit cytotoxic activity against cancer cell, cancer stem cell, tumor cell and the like. Therefore, a medicament containing the cell etc. of the present invention can be used for the prophylaxis or treatment of tumor such as cancer, and can be administered, for example, to mammals (e.g., mouse, rat, hamster, rabbit, cat, dog, bovine, sheep, monkey, human), preferably human. Therefore, in one embodiment of the present invention, the cell etc. of the present invention for use for the prophylaxis or treatment of tumor are provided. In addition, a method for preventing or treating tumor, that includes administering the cell etc. of the present invention preferably in the form of a medicament containing the cell and the like is provided.

Such tumor such as cancer prevented or treated by the medicament of the present invention or the cell etc. of the present invention is described in, for example, "Daniel Baumhoer et al., Am J. Clin Pathol, 2008, 129, 899-906" and the like. Tumor includes benign tumor, malignant tumor (also referred to as "cancer"), and tumor that may be diagnosed or determined to be benign or malignant. Specific examples of tumor include, but are not limited to, liver cancer (e.g., hepatoma), ovarian cancer (e.g., ovary clear cell adenocarcinoma), childhood cancer, lung cancer (e.g., squamous cell carcinoma, small cell lung cancer), testis cancer (e.g., nonseminomas germ cell tumor), soft tissue tumor (e.g., liposarcoma, malignant fibrous histiocytoma), uterine cancer (e.g., cervix intraepithelial tumor, cervix squamous cell carcinoma), melanoma, adrenal gland tumor (e.g., adrenal gland adenoma), neurotic tumor (e.g., schwannoma), gastric cancer (e.g., adenocarcinoma of stomach), renal cancer (e.g., Grawitz tumor), breast cancer (e.g., invasive lobular carcinoma, mucous cancer), thyroid cancer (e.g., medullar cancer), laryngeal cancer (e.g., squamous cell carcinoma), urinary bladder cancer (e.g., invasive transitional cell carcinoma) and the like.

The cells to be contained in the medicament of the present invention may be cultured and/or stimulated using an appropriate medium and/or a stimulating molecule before administration to a subject. Examples of the stimulating molecule include, but are not limited to, cytokines, suitable protein, other components and the like. Examples of the cytokines include IL-2, IL-7, IL-12, IL-15, IFN-γ and the like, and IL-2 can be preferably used. While the concentration of IL-2 in the medium is not particularly limited, for example, it is preferably 0.01 U/ml-$1\times10^5$ U/ml, more preferably 1 U/ml-$1\times10^4$ U/ml. Examples of the suitable protein include CD3 ligand, CD28 ligand, and anti-IL-4 antibody. Besides these, a lymphocyte stimulating factor such as lectin and the like can also be added. Furthermore, serum or plasma may be added to the medium. While the amount of addition to these media is not particularly limited, 0% by volume-20% by volume can be mentioned. In addition, the amount of serum or plasma to be used can be changed according to the culturing stage. For example, serum or plasma concentration can be reduced stepwise. The origin of serum or plasma may be either autologous or allogeneic, and autologous one is preferable from the aspect of safety.

The medicament of the present invention is preferably used by parenteral administration to the subject. Examples of the method for parenteral administration include intravenous, intraarterial, intramuscular, intraperitoneal, and subcutaneous administration and the like. While the dose is appropriately selected according to the condition, body weight, age and the like of the subject, the medicament is generally administered such that the cell number is generally $1\times10^6$-$1\times10^{10}$ cells, preferably $1\times10^7$-$1\times10^9$ cells, more preferably $5\times10^7$-$5\times10^8$ cells, per dose to a subject with body weight 60 kg. The medicament may be administered once, or in multiple divided portions. The medicament of the present invention can be formulated into a known form suitable for parenteral administration, for example, injection or injecting agent. The medicament of the present invention may contain pharmacologically acceptable excipients as appropriate. The medicament of the present invention may contain saline, phosphate buffered saline (PBS), medium and the like to maintain the cells stably. The medium is not particularly limited, and examples thereof include, but are not limited to, media such as RPMI, AIM-V, X-VIVO10 and the like. The medicament may contain a pharmaceutically acceptable carrier (e.g., human serum albumin), preservative and the like for stabilizing purposes.

Furthermore, since the cell etc. of the present invention can kill cells expressing a target antigen such as the aforementioned tumor antigen and the like, it can be used as a killing agent for cells (e.g., cancer cell, cancer stem cell, tumor cell, etc.) expressing the antigen. Such killing agent can be produced and used in the same manner as the aforementioned medicament.

The present invention also includes embodiments of the use of the cell etc. of the present invention in the production of prophylactic or therapeutic agents for tumor, according to the medicament containing the cell etc. of the present invention. Prophylactic or therapeutic agents for tumor can be produced by a method known per se. For example, they can be produced in a known form suitable for parenteral administration, such as injection, injectable agent, or the like, as in the above-mentioned preparation method of the medicament of the present invention.

The present invention is more specifically explained by the following Examples. The scope of the present invention is not limited by the Examples.

EXAMPLES

[Example 1] Study of Production Method of Cell Expressing γδTCR

As a cell population containing hematopoietic progenitor cells, a suspended cell population differentiated from iPS cells (Ff-I01s04 strain: derived from peripheral blood mononuclear cell of healthy individual) provided by the Center for iPS Cell Research and Application, Kyoto University, according to a known method (e.g., methods described in Cell Reports 2(2012)1722-1735 and WO 2017/221975) was used. To be specific, Ff-IO1s04 strain was seeded at $3\times10^5$ cells/well (Day 0) in an ultra-low adhesion-treated 6 well plate, 10 ng/ml BMP4, 50 ng/ml bFGF, 15 ng/ml VEGF, 2 μM SB431542 were added to EB medium (StemPro34 added with 10 μg/ml human insulin, 5.5 μg/ml human transferrin, 5 ng/ml sodium selenite, 2 mM L-glutamine, 45 mM α-monothioglycerol, and 50 μg/ml Ascorbic acid 2-phosphate), and the cells were cultured for 5 days under low-oxygen conditions (5% $O_2$) (Day5). Then, 50 ng/ml SCF, 30 ng/ml TPO, 10 ng/ml FLT-3L were added, and the cells were cultured for 5-9 days (-Day 14) to give a suspended cell population. The medium was changed every two or three days during the culture period. The above-mentioned suspended cell population containing HPC was stained using the following antibody set.

TABLE 1

| | |
|---|---|
| anti-CD34 antibody | Abcam PE/Cy7 |
| anti-CD43 antibody | BD ABC |
| anti-CD45 antibody | BioLegend BV510 |
| anti-CD14 antibody | BioLegend APC/eFluor780 |
| anti-CD235a antibody | BD FITC |

The cell populations that underwent the above-mentioned staining were subjected to sorting by FACSAria. The obtained cell fractions were differentiated into lymphoid cells according to a known method (e.g., the methods described in Journal of Leukocyte Biology 96(2016)1165-1175 and WO 2017/221975). To be specific, the hematopoietic progenitor cell population was seeded at 2000 cells/well in a 48-well-plate coated with Recombinant h-DLL4/Fc chimera (Sino Biological) and Retronectin (Takara Bio Inc.) and cultured under 5% $CO_2$, 37° C. conditions. The medium was changed every two or three days during the culture period. As the medium, αMEM medium added with 15% FBS, 2 mM L-glutamine, 100 U/ml penicillin, 100 ng/ml streptomycin, 55μμ 2-mercaptoethanol, 50 μg/ml Ascorbic acid 2-phosphate, 10 μg/ml human insulin, 5.5 μg/ml human transferrin, 5 ng/ml sodium selenite, 50 ng/ml SCF, 50 ng/ml IL-7, 50 ng/ml FLT-3L, 100 ng/ml TPO, 15 μM SB203580, 30 ng/ml SDF-1α was used. The cells were passaged to a similarly-coated 48-well plate on day 7 and day 14 from the start of the culturing. All cells were collected on day 21 from the start of the culturing (Day 35) and the presence of CD45(+), CD3(+) fractions was confirmed by a flow cytometer (BD FACSAria™ Fusion, manufactured by BD Biosciences). The obtained cells were seeded in a 24-well plate and cultured under 5% $CO_2$, 37° C. conditions. As the medium, αMEM medium added with 15% FBS, 2 mμ L-glutamine, 100 U/ml penicillin, 100 ng/ml streptomycin, 50 μg/ml Ascorbic acid 2-phosphate, 10 μg/ml human insulin, 5.5 μg/ml human transferrin, 5 ng/mL sodium selenite, 500 ng/mL anti-CD3 antibody (OKT3), 10 np dexamethasone (Fuji Pharma: 10171-H02H), 100 U/ml IL-2, 10 ng/mL IL-7. All cells were collected on day 27 from the start of the culturing (Day 41), the cells were counted by a hemocytometer, and stained using the following antibody set.

TABLE 2

| |
| --- |
| Vδ1 Myltenyi FITC |
| Vδ2 Myltenyi APC |
| γδTCR BD BV510 |
| CD3 BioLegend APC/Cy7 |
| αβTCR eBioscience FITC |

As a result of the staining, it was shown that a cell expressing γδTCR (γTCR positive cell) can be prepared from a hematopoietic progenitor cell derived from an iPS cell (Ff-I01s04 strain) (FIG. 1).

Figure 2:
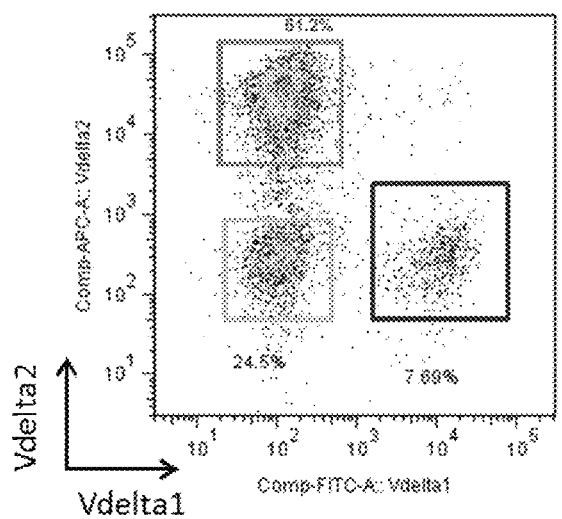
FIG. 2 shows the results of flow cytometry obtained by staining the acquired cells by using an antibody set (Vδ1 Myltenyi FITC, Vδ2 Myltenyi APC, γδTCR BD BV510, CD3 BioLegend APC/Cy7 and αβTCR eBioscience FITC).

Furthermore, since the γδTCR positive cell contains Vδ1 positive γδT cell and Vδ2 positive γδT cell, it was shown that Vδ1 type and VΩ type γδT cells can be prepared (FIG. 2).

[Example 2] Study of Cytotoxic Activity of γδT Cell

The cytotoxic activity of the γδT cell derived from iPS cell (Ff-I01s04 strain) and obtained in Example 1 was evaluated. Using mesothelioma cell line NCI-H226 as a target cell, DELFIA BATDA Reagent (Perkin Elmer) was reacted at 37° C. for 30 min. The reaction mixture was washed, a cell population of γδT cells derived from iPS cells (Ff-I01s04 strain) and containing Vδ1 positive γδT cells and V2 positive γδT cells was mixed at a proportion of 0.5, 1, 2, 4, 8, 16-fold relative to the target cell. The cytotoxic activity of the γδT cells derived from iPS cells (Ff-I01s04 strain) was evaluated based on the target cell death 2 hr later.

Figure 3:
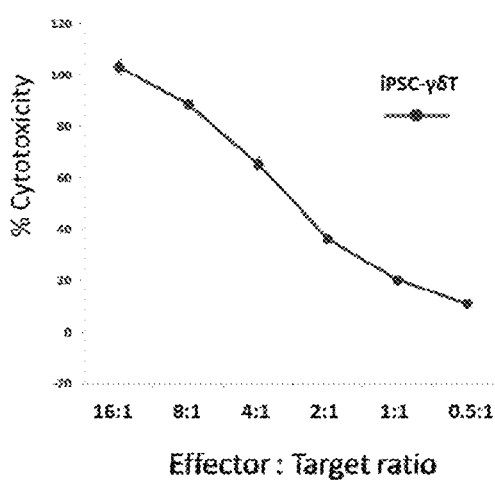
FIG. 3 shows the measurement results of the cytotoxic activity of the acquired γδT cells. The vertical axis shows the cytotoxic activity (%) and the horizontal axis shows the ratio of the number of the mixed γδT cells to the target cell number.

As a result of the evaluation, it was shown that the γδT cell derived from iPS cell (Ff-IO1s04 strain) has a cytotoxic activity against tumor cell line NCI-H226 (FIG. 3).

(Expansion Culture and Function Evaluation of iγδT Cells)

[Example 3] Production of iγδT Cells

By the same method as in Example 1 except that UCHT1 (manufactured by GeneTex) was used as the anti-CD3 antibody, γδT cells (iγδT cells) derived from iPS cells (Ff-I01s04 strain) were produced.

[Example 4] Expansion Culture of iγδT Cells

The iγδT cells obtained in [Example 3] were suspended at 2,000,000 cells/mL in an α-MEM medium containing 15% FBS and an additive containing cytokine in Table 3, seeded on a plate solid-phased with anti-CD3 antibody (UCHT1) and RetroNectin, and cultured at 5% $CO_2$/37° C. for 3 days. On the 3rd day of culture, the cells were collected from the plate, the number of cells was counted using NucleoCounter (registered trade mark) NC-200 (ChemoMetec), and the cells were suspended in an appropriate amount in an α-MEM medium containing 15% FBS and an additive containing cytokine in Table 4, added to a non-immobilized G-Rex (registered trade mark) 6-well plate (WILSON-WOLF), and cultured at 5% $CO_2$/37° C. A part of the cells were collected from the plate 4-6 times on days 5, 6, 7, 8, 9, 10, 11, 14, and 17, and the number of the cells was counted using a hemocytometer.

The anti-CD3 antibody and RetroNectin were immobilized on the culture plate by the following method. The anti-CD3 antibody (UCHT1, final concentration 3000 ng/mL) and RetroNectin (final concentration 150 μg/mL) dissolved in PBS at necessary concentrations were added to the plate and then allowed to stand overnight at 4° C. After washing with PBS, the plate was subjected to the test.

TABLE 3

| product name | manufacturer | Final conc |
| --- | --- | --- |
| Insulin-Transferrin-Selenium Supplements | Invitrogen | 1 x |
| Ascorbic acid 2-phosphate | sigma | 50 μg/ml |
| IL-2 | Peprotech | 15 ng/ml |
| IL-7 | Peprotech | 10 ng/ml |
| IL-15 | Peprotech | 10 ng/ml |
| IL-21 | Peprotech | 20 ng/ml |
| IL-12 | Merck | 50 ng/ml |
| IL-18 | MBL | 50 ng/ml |
| TL-1A | Peprotech | 50 ng/ml |
| Z-VAD-FMK | R&D | 10 μM |
| Human CD30 Antibody | R&D | 300 ng/ml |

TABLE 4

| product name | manufacturer | Final conc |
| --- | --- | --- |
| Insulin-Transferrin-Selenium Supplements | Invitrogen | 1 x |
| Ascorbic acid 2-phosphate | sigma | 50 μg/ml |
| IL-2 | Peprotech | 15 ng/ml |
| IL-7 | Peprotech | 10 ng/ml |
| IL-15 | Peprotech | 10 ng/ml |
| Human CD30 Antibody | R&D | 300 ng/ml |

Figure 4:
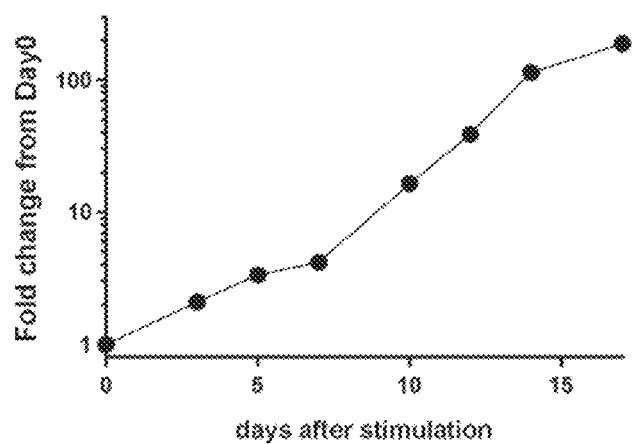
FIG. 4 shows the measurement results of cell proliferation of iPS cell-derived γδT cells (iγδT cells). The vertical axis shows the cell proliferation rate, and the horizontal axis shows the number of days elapsed from the day when stimulation with anti-CD3 antibody (UCHT1) and anti-CD30 antibody was started.

Proliferation of iγδT cells was observed by stimulation with anti-CD3 antibody (UCHT1) and anti-CD30 antibody (FIG. 4).

[Example 5] Production of iPS Cell-Derived Vγ9Vδ2T Cells

1. Preparation of iPS Cell

As the iPS cell, similar to [Example 1], Ff-I01s04 strain provided by the Center for iPS Cell Research and Application (CiRA), Kyoto University, was used. iPS cells were cultured according to the protocol "feeder-free culture of human iPS cells" distributed by CiRA.

2. Differentiation of iPS Cell into HPC

Differentiation of iPS cells into hematopoietic progenitor cells (HPC) was performed according to a known method (WO 2017/221975) as in [Example 1].

3. Vγ9Vδ2 Gene

G115γδT cell clone-derived Vγ9Vδ2 T cell receptor (Vγ9Vδ2TCR G115) was used. As a nucleic acid including a gene encoding Vγ9Vδ2TCR G115, an oligo DNA encoding a polypeptide (SEQ ID NO: 7) designed to align in the order shown in Table 5 from the N-terminal was artificially synthesized.

TABLE 5

| order from N-terminal | gene | amino acid number |
| --- | --- | --- |
| 1 | (G115-derived) TRG | 315 |
| 2 | P2A | 22 |
| 3 | (G115-derived) TRD | 292 |

4. Production of Retrovirus Vector Carrying Vγ9Vδ2 Gene

As the lentivirus vector, pLVSIN-Ub was used in which the sequence encoding the neomycin resistance gene was removed from pLVSIN-CMV Neo (Clontech Laboratories, Inc.) and the CMV promoter was replaced with human ubiquitin promoter. The artificial oligo DNA synthesized in [Example 5] 3. was incorporated into the multi-cloning site of the pLVSIN-Ub retrovirus vector. Using this plasmid and the Lenti-X™ 293T cell line and the Lenti-X™ Packaging Single Shots (VSV-G) of Clontech Laboratories, Inc., a lentiviral vector was produced.

5. Production of iPS Cell-Derived Vγ9Vδ2T Cells

Figure 5:
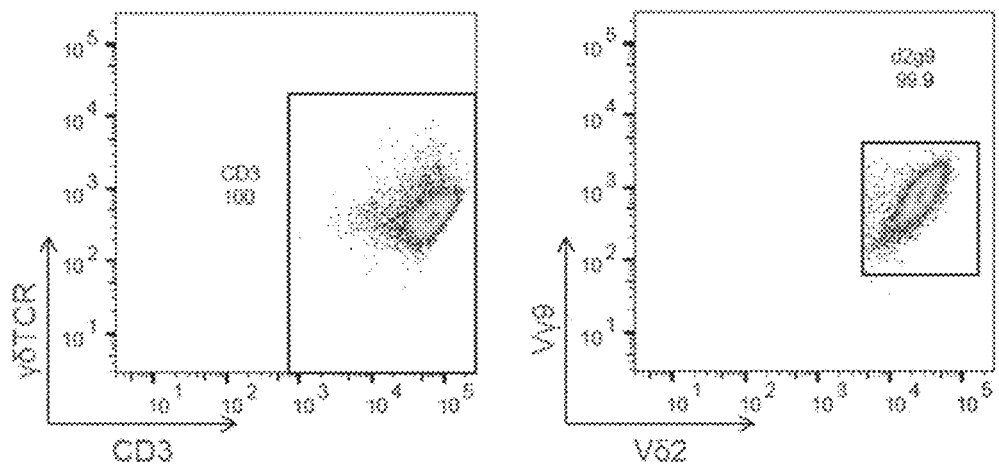
FIG. 5 shows the expression of CD3 and γδTCR molecules on the cell membrane surface of γδT cells (iγ9δ2T cells) differentiated by introducing Vγ9V2TCR gene into iPS cells.
Figure 6:
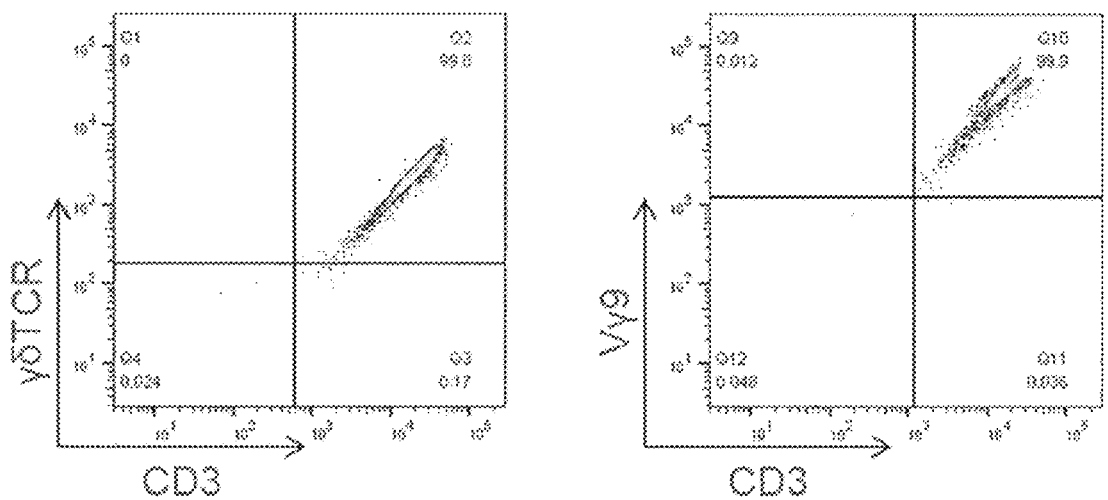
FIG. 6 shows the expression of CD3 and γδTCR molecules on the cell membrane surface of γδT cells (iHγ9δ2T cells) differentiated by introducing Vγ9Vδ2TCR gene into hematopoietic progenitor cells (HPC).

The iPS cells prepared in [Example 5] 1. and the iPS cell-derived hematopoietic progenitor cell (HPC) prepared in Example [Example 5] 2. were infected with the retrovirus vector prepared in [Example 5] 4. carrying Vγ9Vδ2 gene. These cells were differentiated into T cells according to a known method (WO2017/221975) in the same manner as in [Example 1] to prepare iPS cell-derived Vγ9VΩT cells. As the anti-CD3 antibody used in the differentiation step, 500 ng/mL UCHT1 (manufactured by GeneTex) was used. (Hereinafter the iPS cell-derived Vγ9Vδ2T cells prepared from iPS cells are sometimes referred to as "iγδ2T cells", and the iPS cell-derived Vγ9Vδ2T cells prepared from iPS cell-derived HPC are sometimes referred to as "iHγ9δ2T cells".) The obtained iγδ2T cells and iHγ9δ2T cells were measured for the expression of CD3, γδTCR, Vγ9 and V2 on the cell membrane surface with a flow cytometer (BD FACSAria™ Fusion, manufactured by BD Biosciences (FIGS. 5 and 6).

[Example 6] Production of iPS Cell-Derived Anti-CD19-CAR/IL-15γδT Cells

1. Anti-CD19-CAR Gene

As a nucleic acid including anti-CD19-CAR gene, an oligo DNA encoding a polypeptide (SEQ ID NO: 2) designed to align in the order shown in Table 6 from the N-terminal was artificially synthesized.

TABLE 6

| order from N-terminal | gene | amino acid number |
| --- | --- | --- |
| 1 | lead sequence of immunoglobulin in heavy chain | 22 |
| 2 | variable region of anti-CD19 antibody (FMC60) light chain | 104 |
| 3 | GGGGS linker | 15 |
| 4 | variable region of anti-CD19 antibody (FMC60) heavy chain | 120 |

TABLE 6-continued

| order from N-terminal | gene | amino acid number |
| --- | --- | --- |
| 5 | CD8-derived sequence (including transmembrane region) | 83 |
| 6 | intracellular domain region of CD28 | 41 |
| 7 | intracellular domain region of 4-1BB | 47 |
| 8 | intracellular domain region of CD3ζ | 112 |

2. Production of Retrovirus Vector Carrying Anti-CD19-CAR Gene

The artificial oligo DNA synthesized in [Example 6] 1. was incorporated into the multi-cloning site of the pMY retrovirus vector. Using FRY-RD18 cells for retrovirus vector production, a virus vector was produced.

3. IL-15Rα/IL-15 Gene

As a nucleic acid including IL-15Rα/IL-15 genes, an oligo DNA encoding a polypeptide (SEQ ID NO: 6) designed to align in the order shown in Table 7 from the N-terminal was artificially synthesized.

TABLE 7

| order from N-terminal | gene | amino acid number |
| --- | --- | --- |
| 1 | lead sequence of human IL-2 | 23 |
| 2 | C-terminal sequence of human IL-15 | 114 |
| 3 | GGGGS linker | 24 |
| 4 | C-terminal sequence of human IL-15RA | 239 |

4. Production of Retrovirus Vector Carrying IL-15Rα/IL-15 Genes

The artificial oligo DNA synthesized in [Example 6] 3. was incorporated into the multi-cloning site of the pMY retrovirus vector. Using FRY-RD18 cells for retrovirus vector production, a virus vector was produced.

5. Production of iPS Cell-Derived Anti-CD19-CAR/IL-15γδT Cells

The iγδT cells obtained in [Example 4] and the iHγ9δ2T cells produced in [Example 5] 5. were infected with the retrovirus vector carrying anti-CD19-CAR gene produced in [Example 6] 2. and the retrovirus vector carrying IL-15Rα/IL-15 genes produced in [Example 6] 4. to produce iPS cell-derived anti-CD19-CAR/IL-15γδT cells. (Hereinafter the iPS cell-derived anti-CD19-CAR/IL-15γδT cells prepared from iγδT cells are sometimes referred to as "iCD19CAR/IL-15γδT cells", and the iPS cell-derived anti-CD19-CAR/IL-15γδT cells prepared from iHγ9δ2T cells are sometimes referred to as "iHCD19CAR/IL-15γ9δ2T cells").

[Example 7] Expansion Culture of iPS Cell-Derived Anti-Anti-CD19-CAR/IL-15γδT Cells

1. Expansion Culture of iCD19CAR/IL-1518T Cells

By a method similar to that in [Example 4], expansion culture of the iCD19CAR/IL-15γδT cells obtained in [Example 6] was performed. A medium containing an additive containing cytokine in Table 8 instead of the additive containing cytokine in Table 3, and an additive containing cytokine in Table 9 instead of the additive containing cytokine in Table 4 was used.

TABLE 8

| product name | manufacturer | Final conc |
| --- | --- | --- |
| Insulin-Transferrin-Selenium Supplements | Invitrogen | 1 x |
| Ascorbic acid 2-phosphate | sigma | 50 μg/ml |
| IL-7 | Peprotech | 10 ng/ml |
| IL-15 | Peprotech | 10 ng/ml |
| IL-21 | Peprotech | 20 ng/ml |
| IL-12 | Merck | 50 ng/ml |
| IL-18 | MBL | 50 ng/ml |
| TL-1A | Peprotech | 50 ng/ml |
| Z-VAD-FMK | R&D | 10 μM |
| Human CD30 Antibody | R&D | 300 ng/ml |

TABLE 9

| product name | manufacturer | Final conc |
| --- | --- | --- |
| Insulin-Transferrin-Selenium Supplements | Invitrogen | 1 x |
| Ascorbic acid 2-phosphate | sigma | 50 μg/ml |
| IL-7 | Peprotech | 10 ng/ml |
| IL-15 | Peprotech | 10 ng/ml |

Figure 7:
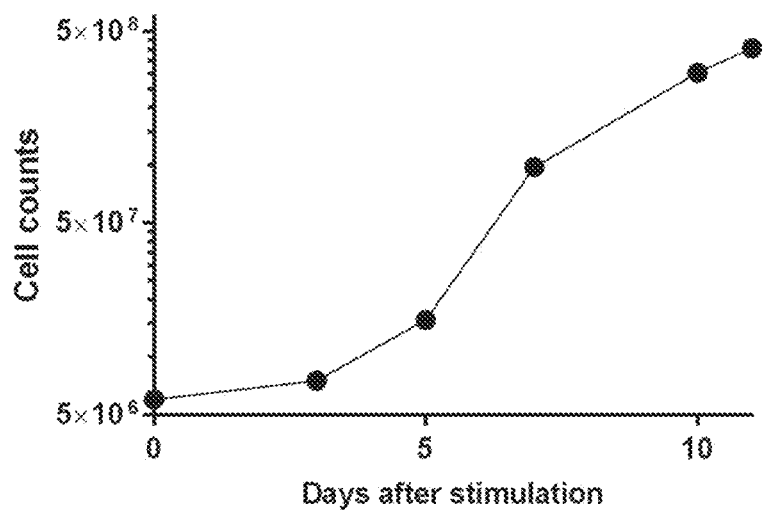
FIG. 7 shows the measurement results of cell proliferation of iγδT cells (iCD19CAR/IL-15γδT cells) expressing anti-CD19-CAR gene. The vertical axis shows the number of cells, and the horizontal axis shows the number of days elapsed from the day when stimulation with anti-CD3 antibody (UCHT1) and anti-CD30 antibody was started.

Proliferation of iCD19CAR/IL-15γδT cells was observed by stimulation with anti-CD3 antibody (UCHT1) and anti-CD30 antibody (FIG. 7).

2. Expansion culture of iHCD19CAR/IL-15γ9δ2T Cells

By a method similar to that in [Example 7] 1., expansion culture of the iHCD19CAR/IL-15γ9δ2T cells obtained in [Example 6] was performed. The anti-human CD30 antibody (human CD30 Antibody) was not added.

Figure 8:
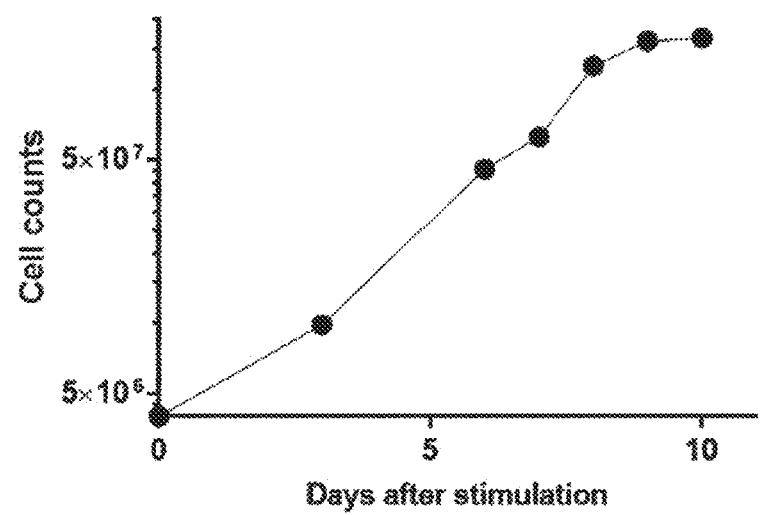
FIG. 8 shows the measurement results of cell proliferation of iHγ9δ2T cells (iHCD19CAR/IL-15γ9δ2T) expressing anti-CD19-CAR gene. The vertical axis shows the number of cells, and the horizontal axis shows the number of days elapsed from the day when stimulation with anti-CD3 antibody (UCHT1) was started.

Proliferation of iHCD19CAR/IL-15γ9δ2T cells was observed by stimulation with anti-CD3 antibody (UCHT1) (FIG. 8).

[Example 8] Study of Cytotoxic Activity of iPS Cell-Derived Anti-CD19-CAR/IL-15γδT Cells The cytotoxic activity of iCD19CAR/IL-15γδT cells and iHCD19CAR/IL-15γ9δ2T cells obtained in [Example 7] was evaluated. Using CD19-positive Raji cell and CD19 negative CCRF-CEN cell as target cells, the iCD19CAR/IL-15γδT cells or iHCD19CAR/IL-15γ9δ2T cells were mixed at a proportion of 0.5, 1, 2, 4, 8, 16-fold relative to the target cell. The cytotoxic activity of the iCD19CAR/IL-15γδT cells and iHCD19CAR/IL-15γ9δ2T cells was evaluated based on the proportion of the target cell death 2 hr later.

Figure 9:
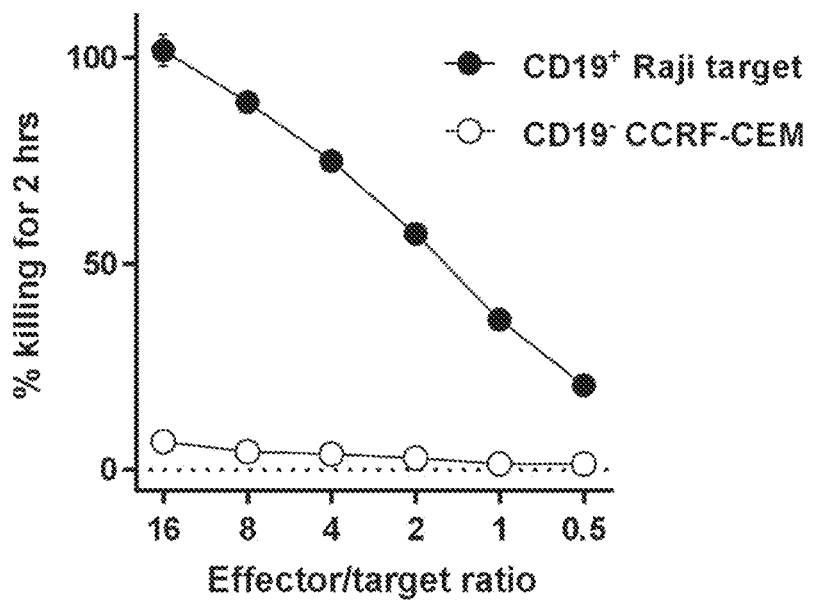
FIG. 9 shows the measurement results of the cytotoxic activity of iγδT cells (iCD19CAR/IL-15γδT cells) expressing anti-CD19-CAR gene. The vertical axis shows the target cell injury rate (%), and the horizontal axis shows the ratio of the number of mixed iCD19CAR/IL-15γδT cells to the number of the target cells.
Figure 10:
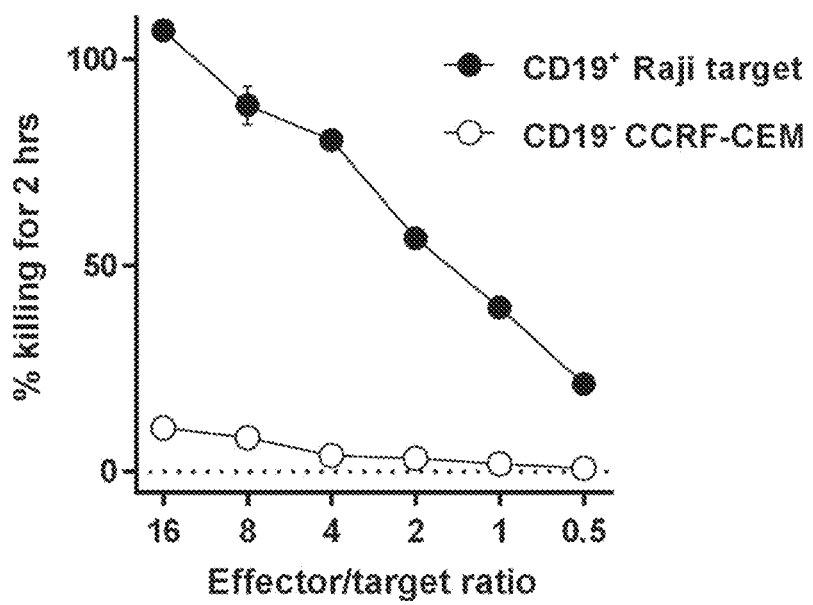
FIG. 10 shows the measurement results of the cytotoxic activity of iHγ9δ2T cells (iHCD19CAR/IL-15γ9δ2T cells) expressing anti-CD19-CAR gene. The vertical axis shows the target cell injury rate (%), and the horizontal axis shows the ratio of the number of mixed iHCD19CAR/IL-15γ9δ2T cells to the number of the target cells.

As a result of evaluation, it was shown that the iCD19CAR/IL-15γδT cells and iHCD19CAR/IL-15γ9δ2T cells have cytotoxic activity against CD19 positive Raji cell, and, do not have cytotoxic activity against CD19 negative CCRF-CEN cell (FIGS. 9 and 10).

[Example 9] Number of Survival Day Extending Effect of iCD19CAR/IL-15γδT Cell $5 \times 10^5$ Nalm6 cells (ATCC) were transplanted to NOD/Shi-scid, IL-2RyKO (NOG) mice (Central Institute for Experimental Animals, female, 7-8-week-old) from the tail vein to prepare Nalm6 xenograft mice. On day 4 post-transplantation, a suspension of iCD19CAR/IL-15γδT cells ($5 \times 10^6$ (cells)) obtained in [Example 6] in 0.1 mL of HBSS-buffer or an equal amount of HBSS-buffer (control) was administered from the tail vein, and the number of days of survival was confirmed.

Figure 11:
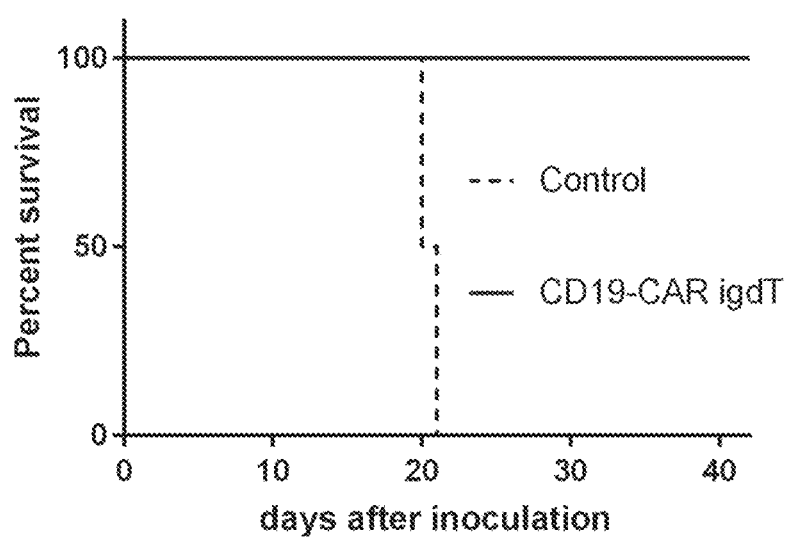
FIG. 11 shows the effect of in vivo administration of iγδT cells (iCD19CAR/IL-15γδT cells) expressing anti-CD19-CAR gene on the number of survival days of human CD19 positive tumor-bearing mouse. The vertical axis shows the survival rate of the mouse, and the horizontal axis shows the number of days elapsed from the day when the cancer cells were transplanted.

All mice transplanted with CD19 positive Nalm6 cancer cells via the tail vein died within 3 weeks in the control administration group, whereas all mice survived for at least 6 weeks in the iCD19CAR/IL-15γδT cell administration group (FIG. 11).

[Example 10] In Vivo Antitumor Effect of iHCD19CAR/IL-15γ9δ2T Cells

Luciferase-expressing Nalm6 cells ($5 \times 10^5$ cells, ATCC) were transplanted to NOD/Shi-scid, IL-2RyKO (NOG) mice (Central Institute for Experimental Animals, female, 7-8-week-old) from the tail vein to prepare luciferase-expressing Nalm6 xenograft mice. On day 4 post-transplantation, a suspension of iHCD19CAR/IL-15γ9δ2T cells ($5 \times 10^6$ (cells)) obtained in [Example 6] in 0.1 mL of HBSS-buffer or an equal amount of HBSS-buffer (control) was administered from the tail vein. Two weeks after administration, luciferin was administered from the tail vein, and the activity of luciferase expressed by Nalm6 cells was measured using the IVIS Imaging System (IVIS LUMINA II, manufactured by CaliperLS).

Figure 12:
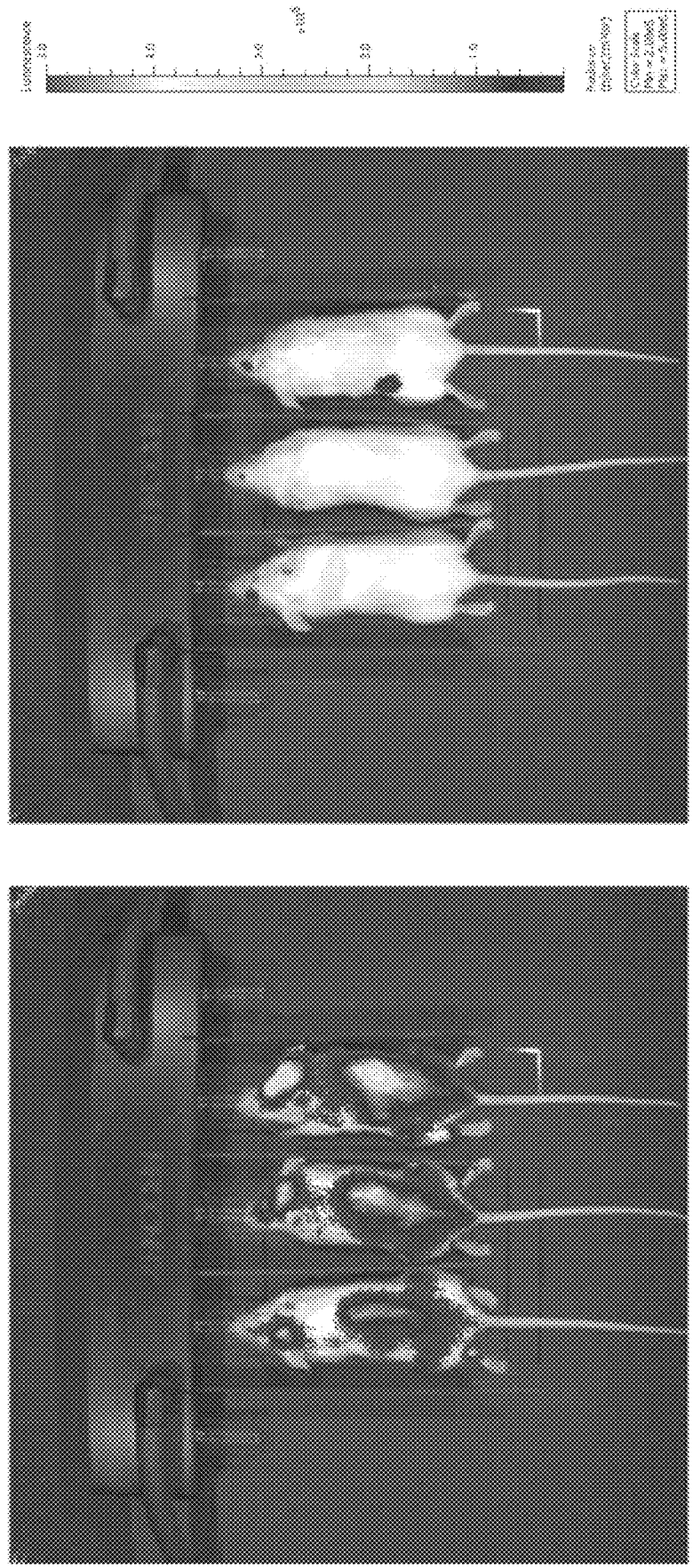
FIG. 12 shows the antitumor effect of in vivo administration of iHγ9δ2T cells expressing anti-CD19-CAR gene (iHCD19CAR/IL-15γ9δ2T) on the luciferase-expressing, human tumor-transplanted mouse.

In the control administered group, luminescence derived from Nalm6 cells was confirmed throughout the body, whereas luminescence was hardly detected in the iHCD19CAR/IL-15γ9δ2T cell administration group (FIG. 12).

INDUSTRIAL APPLICABILITY

According to the present invention, γδT cell can be obtained efficiently, and the cell thus obtained is useful for the prophylaxis or treatment of diseases such as tumor and the like.

This application is based on a patent application No. 2018-133727 filed in Japan (filing date: Jul. 13, 2018) and a patent application No. 2019-117891 filed in Japan (filing date: Jun. 25, 2019), the contents of which are incorporated in full herein.

The invention claimed is:

1. A method for producing a γδT cell from an induced pluripotent stem cell, wherein the induced pluripotent stem cell is derived from a cell other than an αβT cell, wherein the method comprises:
   (1) establishing an induced pluripotent stem cell from a cell other than an αβT cell,
   (2-1) differentiating the induced pluripotent stem cell established in (1) into a hematopoietic progenitor cell,
   (2-2) differentiating the hematopoietic progenitor cell obtained from (2-1) into a T cell without using feeder cells, and
   (3) introducing into any one of the (i) induced pluripotent stem cell obtained from step (1), (ii) a hematopoietic progenitor cell obtained from step (2-1) and (iii) a T cell obtained from step (2-2):
      (a) a nucleic acid encoding a γTCR, and
      (b) a nucleic acid encoding a δTCR.

2. The method according to claim 1, wherein the cell other than an αβT cell is a mononuclear cell other than an αβT cell.

3. The method according claim 1, wherein the cell other than an αβT cell is a monocyte.

4. The method according to claim 1, the method further comprising a introducing into the (i) induced pluripotent stem cell obtained from step (1), (ii) a cell obtained during step (2-1) or step (2-2); and/or (iii) the induced pluripotent stem cell obtained from step (1) comprising the nucleic acid encoding a γTCR and the nucleic acid encoding the δTCR, or a cell obtained during step (2-1) or step (2-2) comprising the nucleic acid encoding a γTCR and the nucleic acid encoding the δTCR,
   a nucleic acid encoding a CAR, which recognizes, and binds to a tumor-specific antigen or a tumor-associated antigen.

5. The method according to claim 1, wherein the γTCR is Vγ9TCR and the δTCR is Vδ2TCR.

6. The method according to claim 1, the method further comprising a introducing a nucleic acid encoding a fusion protein comprising IL-15 and IL-15Rα into the (i) induced pluripotent stem cell obtained from step (1), (ii) a cell obtained during step (2-1) or step (2-2); and/or (iii) the induced pluripotent stem cell obtained from step (1) comprising the nucleic acid encoding a γTCR and the nucleic acid encoding the δTCR, or the T cell obtained in step (2-1) or step (2-2) comprising the nucleic acid encoding the γTCR and the nucleic acid encoding the δTCR.

7. A γδT cell produced by the method according to claim 1.

8. The method according to claim 1, wherein the cell obtained during step (2-2) is an iPSC-derived T cell; or
wherein the cell obtained during step (2-1) is an iPSC-derived hematopoietic progenitor cell.

9. The method according to claim 4, wherein the cell obtained during step (2-2) is an iPSC-derived T cell; or
wherein the cell obtained during step (2-1) is an iPSC-derived hematopoietic progenitor cell.

10. The method according to claim 6, wherein the cell obtained during step (2-2) is an iPSC-derived T cell; or
wherein the cell obtained during step (2-1) is an iPSC-derived hematopoietic progenitor cell.

* * * * *